(12) United States Patent
Mason et al.

(10) Patent No.: US 8,513,397 B2
(45) Date of Patent: Aug. 20, 2013

(54) DNA REPLICON SYSTEM FOR HIGH-LEVEL RAPID PRODUCTION OF VACCINES AND MONOCLONAL ANTIBODY THERAPEUTICS IN PLANTS

(75) Inventors: Hugh S. Mason, Phoenix, AZ (US); Zhong Huang, Tempe, AZ (US); Qiang Chen, Chandler, AZ (US); Charles J. Arntzen, Gold Canyon, AZ (US); Shuo Yuan, Tempe, AZ (US); Brooke Hjelm, Scottsdale, AZ (US)

(73) Assignee: The Arizona Board of Regents for and on behalf of Arizona State University, Scottsdale, AZ (US)

(*) Notice: Subject to any disclaimer, the term of this patent is extended or adjusted under 35 U.S.C. 154(b) by 57 days.

(21) Appl. No.: 13/060,414

(22) PCT Filed: Aug. 27, 2009

(86) PCT No.: PCT/US2009/055237
§ 371 (c)(1),
(2), (4) Date: Apr. 26, 2011

(87) PCT Pub. No.: WO2010/025285
PCT Pub. Date: Mar. 4, 2010

(65) Prior Publication Data
US 2011/0262966 A1    Oct. 27, 2011

Related U.S. Application Data

(60) Provisional application No. 61/092,318, filed on Aug. 27, 2008.

(51) Int. Cl.
*C12N 15/34* (2006.01)
*C12N 15/117* (2010.01)
*C12N 15/13* (2006.01)
*C12N 15/36* (2006.01)
*C12N 15/82* (2006.01)
*C12N 5/10* (2006.01)

(52) U.S. Cl.
USPC ..... 536/23.72; 435/468; 435/419; 435/320.1; 435/69.1; 435/69.3; 435/70.21; 930/220; 930/223

(58) Field of Classification Search
None
See application file for complete search history.

(56) References Cited

U.S. PATENT DOCUMENTS

| | | | | |
|---|---|---|---|---|
| 6,392,121 B1 * | 5/2002 | Mason et al. | ................. | 800/287 |
| 7,217,854 B1 * | 5/2007 | Baulcombe et al. | ........... | 800/278 |
| 2003/0079248 A1 * | 4/2003 | Mason et al. | ................. | 800/280 |

OTHER PUBLICATIONS

Mor Tsafrir, S. et al., "Geminivirius vectors for high-level expression of foreign proteins in plant cells", Biotechnology and Bioengineering—Combinatorial Chemistry, Wiley, New York, NY, US, vol. 81, No. 4, Feb. 20, 2003, pp. 430-437.
Huang, Z., et al., "Rapid, high-level production of hepatitis B core antigen in plant leaf and its immunogenicity in mice", Vaccine, Elsevier Ltd, GB, vol. 24, No. 14, Mar. 24, 2006, pp. 2506-2513.
Voinnet, O., et al., "An enhanced transient expression system in plants based on suppression of gene silencing by the p19 protein of tomatoe bushy stunt virus", The Plant Journal, Blackwell Scientific Publications, Oxford, GB, vol. 33, No. 5, Mar. 1, 2003, pp. 949-956.
Zhong, Huang, et al., A DNA replicon system for rapid high-level production of virus-like particles in plants, Biotechnology and Bioengineering, vol. 103, No. 4, Jul. 1, 2009, pp. 706-714.

* cited by examiner

*Primary Examiner* — David T Fox
*Assistant Examiner* — Steven Bernacki
(74) *Attorney, Agent, or Firm* — Yu Cai; Polsinelli PC

(57) ABSTRACT

Plant viral vectors have great potential in rapid production of proteins, but no simple. Here a geminivirus-based system for high-yield and rapid production of oligomeric protein complexes, including virus-like particle (VLP) vaccines and monoclonal antibodies (mAbs) is described. In particular, a single vector that contains two non-competing replicons for transient expression in *Nicotiana benthamiana* leaves is described. The correct assembly of these subunit proteins into functional oligomeric structures (VLPs or full-size mAb) is also described. This system advances plant transient expression technology by eliminating the need for non-competing viruses, and thus, enhances the realistic commercial application of this technology for producing multiple-subunit protein complexes.

26 Claims, 13 Drawing Sheets

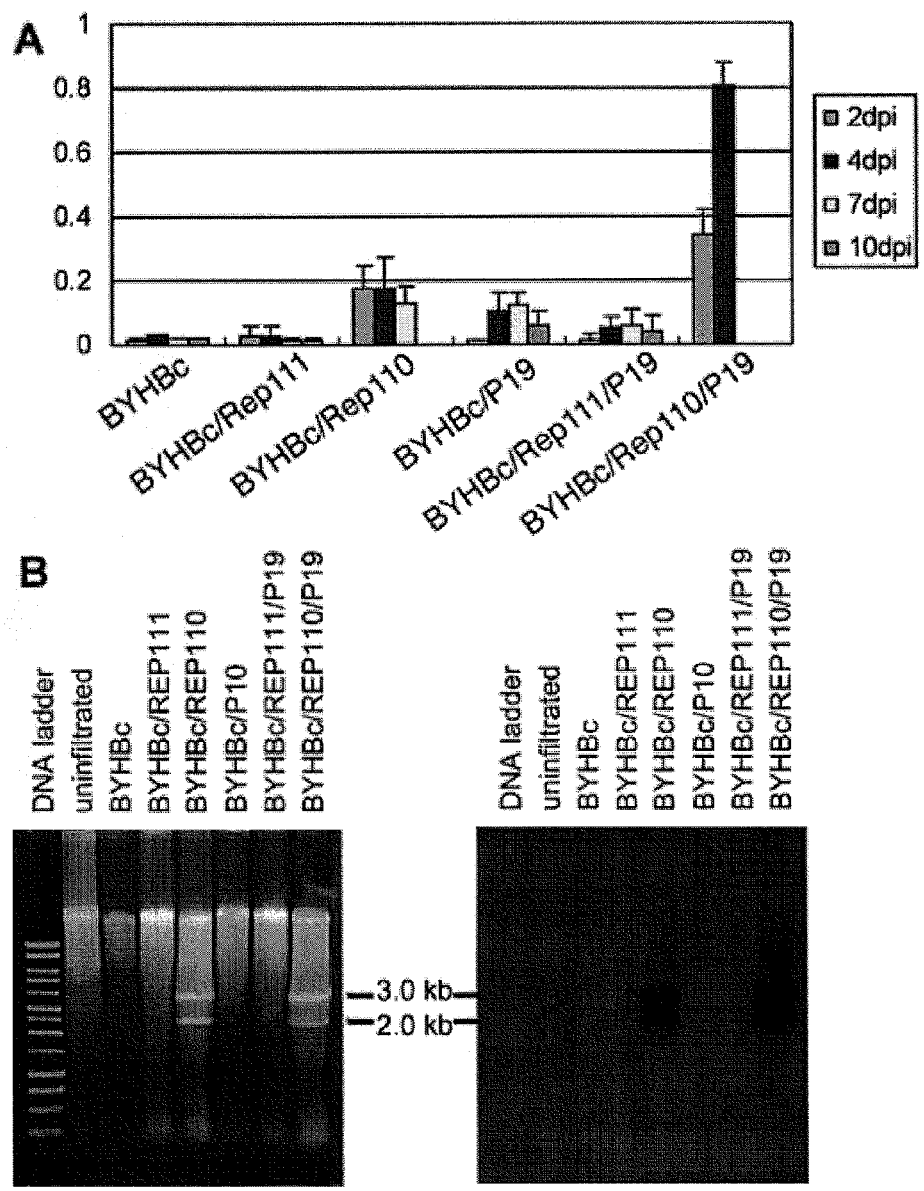

DNA REPLICON SYSTEM FOR HIGH-LEVEL RAPID PRODUCTION OF VACCINES AND MONOCLONAL ANTIBODY THERAPEUTICS IN PLANTS

The present application claims benefit of priority to U.S. Provisional Application Ser. No. 61/092,318 filed Aug. 27, 2008, the entire contents of which are hereby incorporated by reference.

This invention was made with government support under grant numbers 5U01AI061253 and U19-AI-0663332 awarded by the National Institutes of Health. The government has certain rights in the invention.

BACKGROUND OF THE INVENTION

1. Field of the Invention

The present invention relates generally to the fields of genetic engineering of plants using transient gene expression from viral vectors. In particular, the invention relates to the use of vectors using elements of a geminivirus to express a product of interest.

2. Description of Related Art

In recent years, there has been considerable interest in the use of transgenic plants to generate pharmaceutical proteins. A variety of compounds has been successfully expressed in plants, including viral and bacterial antigens and vaccines and as well as many different forms of antibodies (reviewed in Ma et al., 2005; Stoger et al., 2005; Ma et al., 2003). Plants are attractive as protein factories because they can produce large volumes of products efficiently and sustainably and, under certain conditions, can have significant advantages in manufacturing costs (Hood et al., 2001; Giddings, 2001). The possibility of producing therapeutic protein agents on an agricultural scale by "molecular farming" is extremely attractive. In addition to the scalability of the system, one of the major advantages of plants is that they possess an endomembrane system and secretory pathway that are similar to mammalian cells (Vitale and Pedrazzini, 2005). Thus, proteins are generally efficiently assembled with appropriate post-translational modifications. These cost and scale advantages make plant-made pharmaceuticals (PMPs) very promising for both commercial pharmaceutical production and for manufacturing products destined for the developing world.

Pharmaceutical proteins have been produced using transient, viral based expression systems (Canizares et al., 2005; Yusibov et al., 2006) or using stably transformed plants (Giddings et al., 2000; Floss et al., 2007; Twyman et al., 2005). For the latter strategy, the long time frame (months to years) to create stable transgenic plants is a concern for obtaining protein samples for initial pre-clinical studies. In addition, the lack of strong regulatory elements to drive high-level protein accumulation and the position effect associated with the randomness of transgene integration in plant genome still presents challenges for stable transgenic technology. In contrast, the transient systems that are focused on production speed have resolved the difficulty in obtaining the initial research material for testing the function of target pharmaceutical proteins in preclinical trials. For example, a "deconstructed" tobacco mosaic virus (TMV)-based three-component expression system (Marillonnet et al., 2004) allows rapid and high-yield production of vaccine candidates for subsequent immunization and challenge studies (Santi et al., 2006; Huang et al., 2006). Recently, it has been reported that full-size monoclonal antibodies (mAbs) can be rapidly produced at levels as high as 0.5 mg of mAb per gram leaf fresh weight using noncompeting viral vectors derived from TMV and potato virus X (PVX) (Giritch et al., 2006). However, the complexity of requiring five construct modules in total (two modules per subunit plus integrase) for co-expression of both heavy chain and light chain molecules (Giritch et al., 2006) may hinder the practical commercial application of this system. Furthermore, it remains a daunting challenge to find the third or more virus compatible with the existing TMV/PVX expression system to allow efficient co-expression of three or more distinct subunit proteins in same cells, which is required for the production and assembly of some important pharmaceutical complexes such as multi-component virus-like particles (VLPs) (Latham and Galarza, 2001; Pushko et al., 2005) or secretory IgA antibodies. At this point, no plant transient expression system is yet available for efficient expression of heterooligomeric proteins consisting of more than two subunits. Thus, there is a need to develop an advanced transient expression system which consists of minimum number of vectors but still permits high-level expression of multiple subunit proteins.

SUMMARY OF THE INVENTION

The present disclosure overcomes deficiencies in the art by eliminating the difficult task of identifying non-competing virus and needs for co-infection of multiple expression modules, and providing the potential to include genes greater in length than 2.3 kb in the replicons, and thereby enhances the realistic commercial application of this technology for producing multiple-subunit protein complexes.

In certain aspects, the invention provides a method of producing a product in a plant cell comprising obtaining a first nucleic acid segment comprising a promoter and a region encoding a product of interest, wherein the region encoding a product of interest is flanked on either side by at least a portion of a long intergenic region (LIR) of a geminivirus genome; obtaining a second nucleic acid segment comprising a promoter and a nucleic acid encoding a Rep/RepA protein of a geminivirus genome; introducing the first nucleic acid segment and the second nucleic acid segment into a plant cell; and producing the product of interest in the plant cell or a progeny of any generation thereof. As used herein, "a long intergenic region (LIR) of a geminivirus genome" refers to a region of a long intergenic region (LIR) that contains a rep binding site capable of mediating excision and replication by a geminivirus Rep protein. In some embodiments, the first nucleic acid segment may further comprises a short intergenic region (SIR) of a geminivirus genome. As used herein, "a short intergenic region (SIR) of a geminivirus genome" refers to the complementary strand (the short IR (SIR) of Mastreviruses). The nucleic acid segment comprising a product of interest may be any length that can be incorporated into the replicon. In certain embodiments, the nucleic acid segment comprising a product of interest may be between 0.1 kb and 8 kb. In particular embodiments, the nucleic acid segment comprising a product of interest is greater than 2.0, 2.5, 3.0, 3.5, 4.0, 4.5, 5.0, 5.5, 6.0, 6.5, 7.0, or 7.5 kb. In particular embodiments, the nucleic acid segment comprising a product of interest is 2.87 kb. In some embodiments, the method may further comprise isolating the product of interest from the plant cell or a progeny of any generation thereof.

In some embodiments, the first nucleic acid segment and the second nucleic acid segment are comprised in respective first and second vectors. In such embodiments, the first and second vectors may be introduced into the plant cell simultaneously or separately. In other embodiments, the first nucleic acid segment and the second nucleic acid segment are comprised in a single vector.

In particular embodiments, the method may further comprise obtaining a third nucleic acid segment and transfecting the third nucleic acid segment into the plant cell. In some embodiments, the third nucleic acid segment comprises a promoter, at least a portion of a LIR of a geminivirus genome, and a region encoding a product of interest. In particular embodiments, the third nucleic acid segment comprises a promoter and a gene-silencing inhibitor. In one embodiment, the gene-silencing inhibitor is a gene-silencing inhibitor P19 from tomato bushy stunt virus. The method may further comprise isolating the product of interest from the plant cell or a progeny of any generation thereof.

In some embodiments, the first nucleic acid segment, the second nucleic acid segment, and the third nucleic acid segment are comprised in respective first, second, and third vectors. In particular embodiments, the first, second, and third vectors are introduced into the plant cell simultaneously or separately. In other embodiments, the first nucleic acid segment, the second nucleic acid segment, and the third nucleic acid segment are comprised in a single vector.

In particular embodiments, the method further comprises obtaining a third nucleic acid segment comprising a promoter and a region encoding a product of interest, wherein the region encoding a product of interest is flanked on either side by at least a portion of a long intergenic region (LIR) of a geminivirus genome; obtaining a fourth nucleic acid segment comprises a promoter and a gene-silencing inhibitor; and transfecting the third and fourth nucleic acid segment into the plant cell. The method may further comprise isolating the product of interest from the plant cell or a progeny of any generation thereof.

In some embodiments, the first nucleic acid segment, the second nucleic acid segment, the third nucleic acid segment, and the fourth nucleic acid segment are comprised in respective first, second, third, and fourth vectors. In such embodiments, the first, second, third, and fourth vectors are introduced into the plant cell simultaneously or separately. In other embodiments, the first nucleic acid segment, the second nucleic acid segment, the third nucleic acid segment, and the fourth nucleic acid segment are comprised in a single vector.

It is contemplated that the product of interest may be a nucleic acid, protein, polypeptide, or peptide. In certain embodiments, the nucleic acid is an mRNA. In some embodiments, it is contemplated that the protein, polypeptide, or peptide raises an immune response when introduced into an animal.

It is specifically contemplated that the product of interest may be an antigen. In some embodiments, the antigen is from a pathogen or diseased cell. In certain embodiments, the antigen is a viral, bacterial, fungal, or cancer cell-derived antigen. In particular embodiments, the antigen is a hepatitis B core antigen (HBc) or a Norwalk Virus capsid protein (NVCP). In some embodiments, the antigen raises an immune response when introduced into an animal. It is contemplated that the immune response may be protective against a pathogen or disease.

It is further contemplated that the product of interest may be an antibody. In some embodiments, the antibody is a monoclonal antibody. In particular embodiments, the monoclonal antibody is protective against Ebola virus GP1 (6D8).

In some embodiments, the method further comprises incorporating the first and second nucleic acids into a plant cell or a progeny of any generation thereof. In yet further embodiments, the plant cell or a progeny of any generation thereof is stably transformed with the first and second nucleic acids. In still further embodiments, the first and second nucleic acids are comprised in a plasmid within the plant cell or a progeny of any generation thereof.

In further embodiments, the present invention provides a vector system comprising a first nucleic acid segment comprising a promoter and a region encoding a product of interest, wherein the region encoding a product of interest is flanked on either side by at least a portion of a long intergenic region (LIR) of a geminivirus genome, and; a second nucleic acid segment comprising a promoter and a nucleic acid encoding a Rep/RepA protein of a geminivirus genome.

In still further embodiments, the invention provides a plant comprising a first nucleic acid segment comprising a promoter and a region encoding a product of interest, wherein the region encoding a product of interest is flanked on either side by at least a portion of a long intergenic region (LIR) of a geminivirus genome; and a second nucleic acid segment comprising a promoter and a nucleic acid encoding a Rep/RepA protein of a geminivirus genome.

It is contemplated that any embodiment discussed in this specification can be implemented with respect to any method or composition of the invention, and vice versa. Furthermore, compositions of the invention can be used to achieve methods of the invention.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be better understood by reference to one or more of these drawings in combination with the detailed description of specific embodiments presented herein.

(FIG. 3A) Quantification of HBc expression by different vector combinations; (FIG. 3B) and (FIG. 3C) Replicon formation demonstrated by Southern blotting of plant DNA from infiltrated leaves; (FIG. 3D) Northern blotting analysis of plant RNA from infiltrated leaves.

(FIG. 4A) Western blot analysis of the HBc from infiltrated N. benthamiana leaves. Protein samples were run on a 12% SDS-PAGE and blotted onto a PVDF membrane. The membrane was then probed with a mouse monoclonal anti-HBc which recognizes amino acid residues 130-140 of HBc. (FIG. 4B) Sucrose gradient analysis. Extract from BYHBc/REP110/P19 infiltrated N. benthamiana leaves and E. coli-derived HBc (e-HBc) were layered onto 10-50% sucrose gradients and subjected to centrifugation as described in Materials and Methods. Ten fractions (0.5-ml each) were taken from top to bottom and assayed by HBc ELISA. (FIG. 4C) Dot blot of sucrose gradient fractions probed with rabbit polyclonal anti-HBc. (FIG. 4D) and (FIG. 4E), Electron microscopy. Partially purified HBc were negatively stained with 0.5% uranyl acetate and visualized by transmission electron microscopy. Bar=50 nm.

(FIG. 5A) A time course of NVCP expression by different vector combinations. Data reported are means±S.D. from four independently infiltrated samples. (FIG. 5B) Western blot for NVCP expression. Lane 1, insect-derived NVCP standard, respectively; lane 2, 3, and 4 are uninfiltrated, BYGFP-infiltrated and BYNVCP-infiltrated leaf extracts, respectively. (FIG. 5C) Sucrose gradient profile of insect-derived and plant-expressed NVCP as analyzed by a polyclonal ELISA assay.

(FIG. 6A) and (FIG. 6B) mixture of protoplasts from leaves infiltrated separately with BYGFP/REP110/P19 or BYDsRed/REP110/P19. (FIG. 6C) and (FIG. 6D), protoplasts from leaves infiltrated with BYGFP/BYDsRed/REP110/P19. (FIG. 6E) and (FIG. 6F), protoplasts from leaves infiltrated with BYGFPDsRed.R. FIGS. 6A, C and E are viewed with a GFP filter; FIGS. 6B, D and F are viewed with a DsRed filter.

(FIG. 7A) Expression of 6D8. N. benthamiana leaves were either co-infiltrated with separate vectors for light chain (pBY-L(6D8)) or heavy chain (pBY-H(6D8)), REP110 and P19, or infiltrated with a single vector harboring replicons for light, heavy chain and Rep (pBY-HL(6D8).R). Leaves were also infiltrated with a construct encoding the mRNA silencing inhibitor P19 as a negative control. Protein extracts were analyzed with ELISA which detects the assembled form of 6D8 mAb (see Methods). (FIG. 7B) Western blot analysis of plant-derived 6D8 under reducing condition. Protein samples were separated on a 4-12% SDS-PAGE gradient gel under denaturing and reducing condition and blotted onto a PVDF membrane. The membrane was incubated with a goat anti-human gamma chain antibody or goat anti-human kappa chain antibody to detect heavy chain (FIG. 7B1) or light chain (FIG. 7B2). Lane 1, Protein samples extracted with un-infiltrated leaves; lane 2, human IgG as a reference standard; lane 3, Protein sample extracted from the leaves co-infiltrated with separate replicons for light chain (pBY-L(6D8)) and heavy chain (pBY-H (6D8)); lane 4, Protein extracted from the single vector pBY-HL(6D8).R infiltrated leaves. (FIG. 7C) Western blot analysis under non-reducing condition. Protein samples were separated on a 4-12% SDS-PAGE gradient gel under non-reducing condition. The membrane was then incubated with a goat anti-human kappa chain specific antibody. Lane 1, Protein samples extracted with un-infiltrated leaves; lane 2, human IgG as a reference standard; lane 3, Protein sample extracted from the leaves co-infiltrated with separate replicons for light chain (pBY-L(6D8)) and heavy chain (pBY-H(6D8)). $H_2L_2$, fully assembled IgG heterotetramer with two heavy chains and two light chains. $H_2L$, heterotrimer with two heavy chains and one light chain assembled; HL, heterodimer with one light chain and heavy chain; $L_2$, two light chain homodimer.

DETAILED DESCRIPTION OF ILLUSTRATIVE EMBODIMENTS

Figure 1:
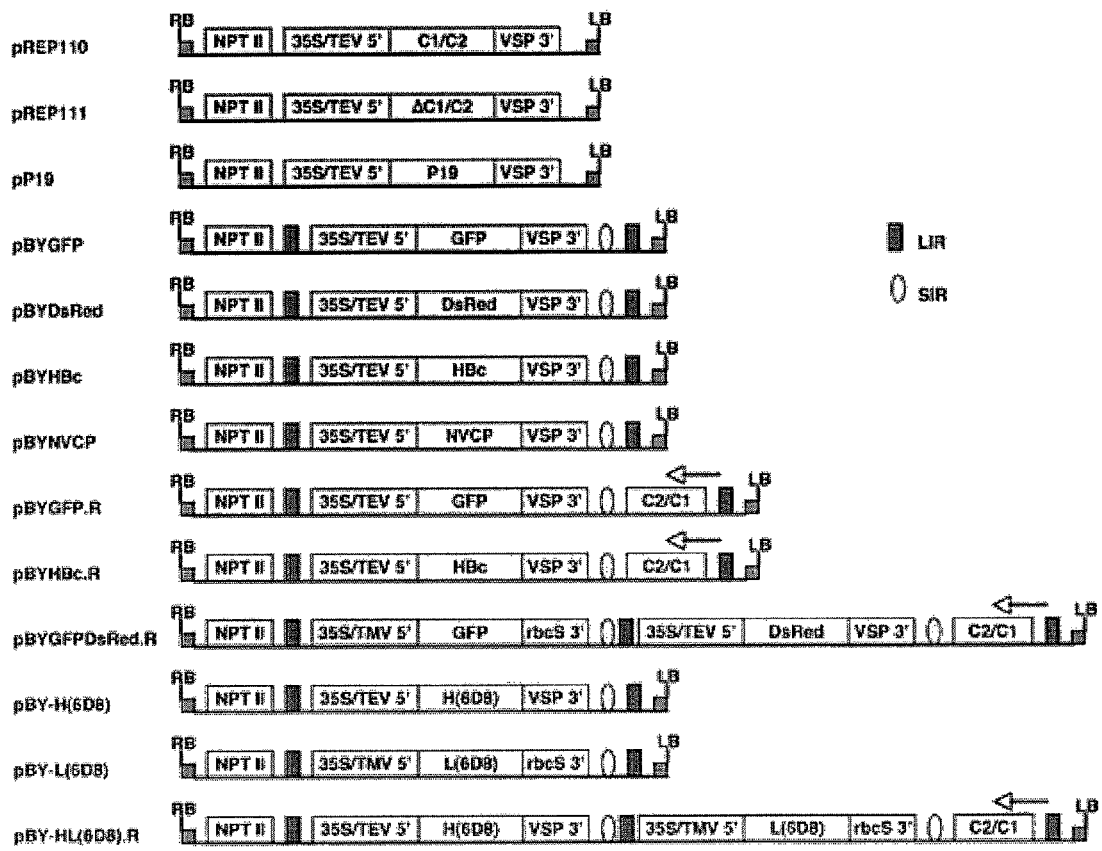
FIG. 1 Schematic representation of the T-DNA region of the vectors used in this study. 35S/TEV 5', CaMV 35S promoter with tobacco etch virus 5' UTR; 35S/TMV 5', CaMV 35S promoter with tobacco mosaic virus 5' UTR; VSP 3', soybean vspB gene 3' element; rbcS 3', pea rbcS gene 3' element, NPT II, expression cassette encoding nptII gene for kanamycin resistance; LIR, long intergenic region of BeYDV genome; SIR, short intergenic region of BeYDV genome; C1/C2, BeYDV ORFs C1 and C2, encoding replication initiation protein (Rep) and RepA; ΔC1/C2, intron-deleted C1 and C2 encoding Rep only; LB and RB, the left and right borders of the T-DNA region. Arrows indicate direction of transcription of C1/C2 gene.

As discussed in Arntzen et al. (2005), there have been two dominate strategies for the expression of antigens in plants— stable transgenic gene expression and transient expression with viral vectors. While transient expression systems such as the one presented here provide a speedy solution to provide material for initial characterization, stable transgenic plants hold the most promising scalability when extraordinarily large amount of plant made pharmaceutical (PMP) production is needed. For both the stable and transient systems, mRNA accumulation is a bottleneck in protein expression. However, the stable transgenic technology is further complicated by the "position effect"—the mRNA level depends on the position in which the transgene inserted in the chromosome (Matzke and Matzke, 1998). As a result, finding a highly-expressing transgenic line becomes a statistical exercise, in which hundreds or even thousands of plants must be screened to identify outliers expressing at high levels.

This invention provides a viral replicon-based, vector transient expression system and its application in high-yield rapid production of oligomeric protein complexes of pharmaceutical importance, including VLP vaccines and mAbs in plants. First, a three-component vector system, consisting of one replicon vector, one Rep/Rep A supplying vector and one silencing-suppressor vector, was demonstrated as allowing extremely efficient replicon formation and high-level accumulation of target mRNA and protein. Next it was shown that the replicon system is non-competing, allowing simultaneous expression of two subunit proteins. More significantly, a single vector has been designed which contains multiple replicon cassettes, and it has been found that it was as efficient as the three-component system in directing expression of two oligomeric protein molecules. Using the replicon vectors, high-level expression and correct assembly of two VLP vaccine antigens, hepatitis B core antigen (HBc) and Norwalk Virus capsid protein (NVCP), and one protective MAb against Ebola virus GP1(6D8) (Wilson et al., 2000) was obtained within 4 to 7 days post infiltration (dpi) of *Nicotiana benthamiana* leaves. The system, therefore, represents the most advanced plant transient expression technology and eliminates the difficult task of identifying a non-competing virus and the need for co-infection of multiple expression modules, thereby enhancing the realistic commercial application of this technology for producing multiple-subunit protein complexes.

I. GEMINIVIRUSES

The geminiviruses are a large and diverse family of plant DNA viruses, with circular single-stranded (ss) DNA genomes that replicate through circular double stranded DNA intermediates. See Hanley-Bowdoin et al. (1999); Lazarowitz (1992); Timmermans et al. (1994).

In particular, the geminiviruses replicate via a rolling circle mechanism, analogous to that used by ssDNA plasmids of gram positive microorganisms. The only exogenous protein required for replication is the viral replication initiation (Rep) protein encoded by a geminiviral replicase gene. This multi-functional protein initiates replication at a conserved stem loop structure found in the viral origin of replication by inducing a nick within a conserved nonanucleotide motif (TAATATTA↓C) found in the intergenic loop sequence. Transcription of the viral genome is bidirectional with transcription initially within the intergenic (IR) region. Rep also has functions involved in controlling the plant cell cycle, and possibly also in modulating the expression of host genes involved in DNA replication (reviewed by Palmer et al., 1997b). The Rep protein can act in trans, that is, it need not be expressed by the viral replicon itself, but can be supplied from another extrachromosomal viral replicon, or even from a nuclear transgene (Hanley-Bowdoin et al., 1990). The cis requirements for viral replication are the viral intergenic region/s (IR), which contain sequences essential for initiation of rolling circle replication (the long intergenic region (LIR) of Mastreviruses, or the intergenic region of other geminiviruses) and synthesis of the complementary strand (the short IR (SIR) of Mastreviruses).

The unique nicking function of the Rep protein of geminiviruses (Laufs et al., 1995a; Laufs et al., 1995b) allows for replicative release of recombinant viral DNA cloned between a tandem repeat of the LIR from a chromosome-integrated site (Hayes et al., 1988; Grimsley et al., 1987; Kanevski et al., 1992). The DNA then replicates episomally in the nucleus. These characteristics of geminivirus replicons will enable development of stable transgenic vectors in which the episomal replication nature and high copy number of geminivirus replicons would eliminate position effect of transgene expression, as well as ensure a high target protein expression level in stable transformed plants. A previous study has indeed shown that an earlier version the Bean Yellow Dwarf Virus derived vector and co-expressed with Rep driven by an inducible promoter in stable transgenic potato produced an 80-fold increase in mRNA and a 10-fold increase in transgenic protein expression (Zhang and Mason, 2006). This evidence further supports the likelihood of success in using the current improved version of replicons to develop high-expressing stable transgenic vectors for large-scale PMP production. The utilization of the advanced replicon vectors in both transient and stable transgenic technologies will thus allow a rapid assessment of pharmaceutical candidates and a scalable platform for commercial production.

II. NUCLEIC ACIDS

This invention is directed to plant expression vectors comprising one or more vectors comprising a first nucleic acid segment comprising a promoter and a region encoding a product of interest, wherein the region encoding a product of interest is flanked on either side by at least a portion of a long intergenic region (LIR) of a geminivirus genome, and; a second nucleic acid segment comprising a promoter and a nucleic acid encoding a Rep/RepA protein of a geminivirus genome. The vectors may also comprise various additional components, including but not limited to those described above.

The term "nucleic acid" is well known in the art. As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

All types of genes may be expressed by the vector systems of the present invention. In this respect, the term "gene," "polynucleotide," or "nucleic acid" is used for to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs of a polypeptide of the invention. It also is contemplated that a particular polypeptide may be encoded by nucleic acids containing variations having slightly different nucleic acid sequences but, nonetheless, encode the same or substantially similar protein.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

It is contemplated that the nucleic acid constructs of the present invention may encode full-length polypeptide from any source or encode a truncated version of the polypeptide such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to a particular gene, such as the product of interest. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass biologically functional equivalent modified polypeptides and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

It also will be understood that this invention is not limited to the particular nucleic acid and amino acid sequences of the polynucleotide encoding the product of interest. Recombinant vectors and isolated DNA segments may therefore variously include the coding regions of the product of interest themselves, coding regions bearing selected alterations or modifications in the basic coding region, or they may encode larger polypeptides that nevertheless include coding regions of the product of interest or may encode biologically functional equivalent proteins or peptides that have variant amino acids sequences.

If desired, one also may prepare fusion proteins and peptides, e.g., where the coding regions of the product of interest are aligned within the same expression unit with other proteins or peptides having desired functions, such as for purification or immunodetection purposes (e.g., proteins that may be purified by affinity chromatography and enzyme label coding regions, respectively).

Encompassed by certain embodiments of the present invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length published sequences for the product of interest.

Encompassed by certain embodiments of the invention are DNA segments encoding functional nucleic acid molecules, for example hybridization probes; amplification primers; siRNA, RNAi or antisense molecules; ribozymes; or RNA aptamers. In particular embodiments these functional nucleic acid molecules are identical or complementary to all or part of a nucleic acid sequence encoding the amino acid sequence of a product of interest. In other embodiments these functional nucleic acid molecules are identical or complementary to non-coding regions transcript of a product of interest or to nucleic acid "control sequences" that are required for the efficient expression of RNA or protein of a product of interest.

These definitions generally refer to a single-stranded molecule, but in specific embodiments will also encompass an additional strand that is partially, substantially or fully complementary to the single-stranded molecule. Thus, a nucleic acid may encompass a double-stranded molecule that comprises complementary strands or "complements" of a particular sequence comprising a molecule. In particular aspects, a nucleic acid encodes a protein or polypeptide, or a portion thereof.

A. Nucleic Acid Vectors

In particular embodiments, the invention concerns isolated DNA segments and recombinant vectors incorporating DNA sequences that encode a product of interest. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated that control sequences which direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include control sequences associated with the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), human platelet endothelial cell adhesion molecule-1 (Almendro et al., 1996), and the SM22α promoter.

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'—methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

4. Termination Signals

The vectors or constructs of the present invention will generally comprise at least one termination signal. A "termination signal" or "terminator" is comprised of the DNA sequences involved in specific termination of RNA transcription by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that the terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

5. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the soybean vegetative storage protein (vspB) polyadenylation signal and/or pea RuBP carboxylase small subunit (rbcS) polyadenylation signal, convenient and/or known to function well in various plant target cells. Polyadenylation may increase the stability of the transcript or may facilitate cytoplasmic transport.

6. Origins of Replication

In order to propagate a vector in a host cell, it may contain one or more origin of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose selection is based on colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

Vectors of the invention may be used in a host cell to produce a product of interest. The particular, the vectors of the current invention may be a plant cell. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding or functional nucleic acid encoding sequence, is transferred or introduced into the host cell. A transformed cell includes the primary subject cell and its progeny.

Host cells may be derived from prokaryotes or eukaryotes, including plant cells, yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, Sf9, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

1. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubinstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986). Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubinstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubinstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

D. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952, 500, each incorporated herein by reference); or by desiccation/inhibition-mediated DNA uptake (Potrykus et al., 1985).

Through the application of techniques such as these, organelle(s), cell(s), tissue(s) or organism(s) may be stably or transiently transformed.

E. Preparation of Nucleic Acids

One aspect of the present invention concerns isolated nucleic acid segments and their use in producing a product of interest in a plant cell. In certain embodiments, the present invention concerns nucleic acids encoding the proteins, polypeptides, peptides of the invention. A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816, 571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

F. Purification of Nucleic Acids

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

A nucleic acid may be purified on polyacrylamide gels, cesium chloride centrifugation gradients, chromatography columns or by any other means known to one of ordinary skill in the art (see for example, Sambrook et al., 2001, incorporated herein by reference). In some aspects, a nucleic acid is a pharmacologically acceptable nucleic acid. Pharmacologically acceptable compositions are known to those of skill in the art, and are described herein.

G. Nucleic Acid Detection

1. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M $NaHPO_4$, 7% sodium dodecyl sulfate (SDS), 1 mM EDTA at 65° C., and washing in 0.1×SSC/0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the SOD1 gene locus, variants and fragments thereof are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCTAJS89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329 822 disclose a nucleic acid amplification process involving cyclically synthesizing single-stranded RNA ("ssRNA"), ssDNA, and double-stranded DNA (ds-DNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

III. PROTEINACEOUS COMPOSITIONS

It is contemplated that the product of interest may be a nucleic acid, protein, polypeptide, or peptide. The product of interest may include, but are not limited to, an antigen or an antibody. Examples of antigens include, but are not limited to, a hepatitis B core antigen (HBc) or a Norwalk Virus capsid protein (NVCP). Examples of antibodies include, but are not limited to, monoclonal antibodies.

In certain embodiments the product of interest is a protein, polypeptide or peptide. As used herein, a "protein," "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate an immune response. The terms described above may be used interchangeably. A "modified protein" or "modified polypeptide" refers to a protein or polypeptide whose chemical structure, particularly its amino acid sequence, is altered with respect to the wild-type protein or polypeptide. It is specifically contemplated that a modified protein or polypeptide may be altered with respect to one activity or function yet retain a wild-type activity or function in other respects, such as immunogenicity.

In certain embodiments the size of a protein or polypeptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be know to those of ordinary skill in the art.

A. Protein Purification

It may be desirable to purify or isolate the protein of interest. Protein purification techniques are well known to those of skill in the art. These techniques involve, at one level, the crude fractionation of the cellular milieu to polypeptide and non-polypeptide fractions. Having separated the polypeptide from other cellular components, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; affinity chromatography; polyacrylamide gel electrophoresis; and isoelectric focusing. A particularly efficient method of purifying peptides is fast protein liquid chromatography or even HPLC.

The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., altering pH, ionic strength, and temperature).

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

B. Protein detection

The protein of interest may be detected by any means known to those of skill in the art, including but not limited to those described below.

1. Immunodetection Methods

As discussed, in some embodiments, the present invention concerns immunodetection methods for binding, purifying, removing, quantifying and/or otherwise detecting biological components such as a protein of interest. The immunodetection methods of the present invention can be used to identify antigenic regions of a protein of interest that have therapeutic implications.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle et al., 1999; Gulbis et al., 1993; De Jager et al., 1993; and Nakamura et al., 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

These methods include methods for purifying a protein, polypeptide and/or peptide from organelle, cell, tissue or organism's samples. In these instances, the antibody removes the antigenic protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an antigen or antigenic domain, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the antibody/antigen complex. In this method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

a. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with antibodies. After binding and/or washing to remove non-specifically bound immune complexes, the bound antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

b. Immunohistochemistry

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize the protein of interest or to evaluate the amount the protein of interest in a cell. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Immunohistochemistry or IHC refers to the process of localizing proteins in cells of a tissue section exploiting the principle of antibodies binding specifically to antigens in biological tissues. It takes its name from the roots "immuno," in reference to antibodies used in the procedure, and "histo," meaning tissue. Immunohistochemical staining is widely used in the diagnosis and treatment of cancer. Specific molecular markers are characteristic of particular cancer types.

Visualizing an antibody-antigen interaction can be accomplished in a number of ways. In the most common instance, an antibody is conjugated to an enzyme, such as peroxidase, that can catalyse a colour-producing reaction. Alternatively, the antibody can also be tagged to a fluorophore, such as FITC, rhodamine, Texas Red, Alexa Fluor, or DyLight Fluor. The latter method is of great use in confocal laser scanning microscopy, which is highly sensitive and can also be used to visualize interactions between multiple proteins.

Briefly, frozen-sections may be prepared by rehydrating 50 mg of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

There are two strategies used for the immmunohistochemical detection of antigens in tissue, the direct method and the indirect method. In both cases, the tissue is treated to rupture the membranes, usually by using a detergent, such as Triton X-100.

The direct method is a one-step staining method, and involves a labeled antibody (e.g. FITC conjugated antiserum) reacting directly with the antigen in tissue sections. This technique utilizes only one antibody and the procedure is therefore simple and rapid. However, it can suffer problems with sensitivity due to little signal amplification and is in less common use than indirect methods.

The indirect method involves an unlabeled primary antibody (first layer) which reacts with tissue antigen, and a labeled secondary antibody (second layer) which reacts with the primary antibody. This method is more sensitive due to signal amplification through several secondary antibody reactions with different antigenic sites on the primary antibody. The second layer antibody can be labeled with a fluorescent dye or an enzyme.

In a common procedure, a biotinylated secondary antibody is coupled with streptavidin-horseradish peroxidase. This is reacted with 3,3'-Diaminobenzidine (DAB) to produce a brown staining wherever primary and secondary antibodies are attached in a process known as DAB staining. The reaction can be enhanced using nickel, producing a deep purple/gray staining.

The indirect method, aside from its greater sensitivity, also has the advantage that only a relatively small number of standard conjugated (labeled) secondary antibodies needs to be generated. For example, a labeled secondary antibody raised against rabbit IgG, which can be purchased "off the shelf," is useful with any primary antibody raised in a rabbit. With the direct method, it would be necessary to make custom labeled antibodies against every antigen of interest.

c. Protein Arrays

Protein array technology is discussed in detail in Pandey and Mann (2000) and MacBeath and Schreiber (2000), each of which is herein specifically incorporated by reference.

These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a protein of interest.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

C. Protective Immunity

In some embodiments of the invention, the protein of interest can raise an immune response in a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide refers to a stretch of amino acids covalently linked there amongst via peptide bonds. Different polypeptides have different functionalities according to the present invention. While according to one aspect a polypeptide is derived from an immunogen designed to induce an active immune response in a recipient, according to another aspect of the invention, a polypeptide is derived from an antibody which results following the elicitation of an active immune response, in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity.

As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to staphylococcus bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge from the composition ("hyperimmune globulin"), that contains antibodies directed against Staphylococcus or other organism. A subject thus treated would donate plasma from which hyperimmune globulin would then be obtained, via conventional plasma-fractionation methodology, and administered to another subject in order to impart resistance against or to treat staphylococcus infection. Hyperimmune globulins according to the invention are particularly useful for immune-compromised individuals, for individuals undergoing invasive procedures or where time does not permit the individual to produce his own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T– cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

In order to produce monoclonal antibodies, hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then be cultured, in bulk, and the monoclonal antibodies harvested from the culture media for use. By definition, monoclonal antibodies are specific to a single epitope. Monoclonal antibodies often have lower affinity constants than polyclonal antibodies raised against similar antigens for this reason.

Monoclonal antibodies may also be produced ex-vivo by use of primary cultures of splenic cells or cell lines derived from spleen. In order to produce recombinant antibody (see generally Huston et al., 1991; Johnson et al., 1991; Mernaugh et al., 1995), messenger RNAs from antibody producing B-lymphocytes of animals, or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. For a general discussion of conjugation of fluorescent or enzymatic moieties see Johnstone et al. (1982). The binding of antibodies to a solid support substrate is also well known in the art (Harlow et al., 1988; Borrebaeck, 1992).

As used herein and in the claims, the phrase "an immunological portion of an antibody" include a Fab fragment of an antibody, a Fv fragment of an antibody, a heavy chain of an antibody, a light chain of an antibody, an unassociated mixture of a heavy chain and a light chain of an antibody, a heterodimer consisting of a heavy chain and a light chain of an antibody, a catalytic domain of a heavy chain of an antibody, a catalytic domain of a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

IV. EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

I. Results

Agrobacterium-mediated co-delivery of a replicon vector and a Rep/RepA-supplying vector into plant leaf leads to efficient replicon formation and high-level protein production.

Figure 2:
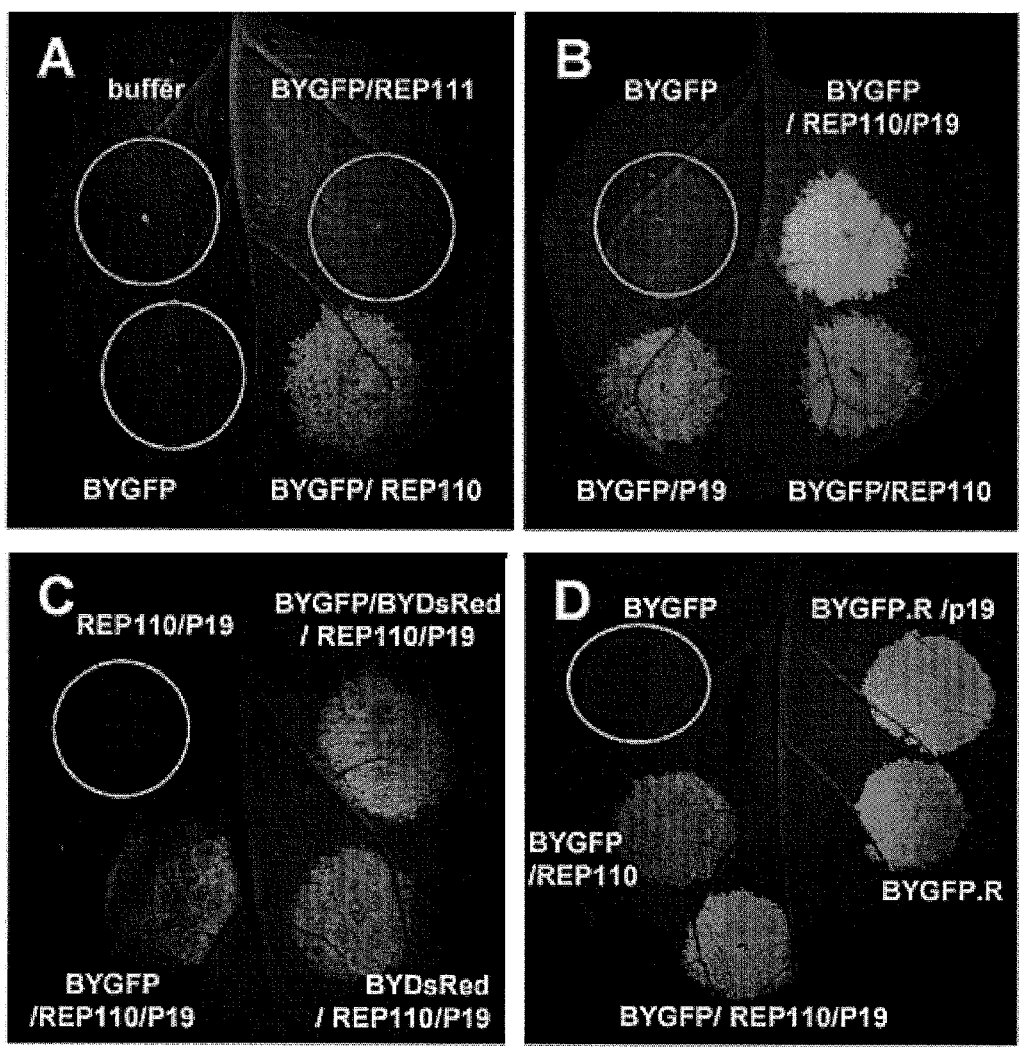
FIG. 2 Visualization of GFP and/or DsRed expression in plant leaves. N. benthamiana leaves were infiltrated with a single Agrobacterium strain or mixtures of strains harboring expression vectors as indicated. Infiltrated leaves were examined at 5 days post infiltration (dpi) with handheld UV lamps as described in Materials and Methods.

It was previously shown that formation of bean yellow dwarf virus (BeYDV)-based replicons in bombarded tobacco NT-1 cells resulted in increased transient expression of target proteins (Mor et al., 2003). To develop a scalable high-yield transient expression system, it was first tested if Agrobacterium-mediated delivery of replicon vectors into plant leaf can lead to replicon formation and increased target protein expression. N. benthamiana leaves were infiltrated with an Agrobacterium culture containing a replicon vector pBYGFP (FIG. 1) encoding the green fluorescent protein, or co-infiltrated with a mixture of two Agrobacterium cultures containing pBYGFP and one of the Rep-supplying vectors (pREP110 encoding both Rep and RepA or pREP111 encoding Rep only, FIG. 2). At 5 days post infiltration (dpi), very faint green fluorescence was observed from leaf areas infiltrated with pBYGFP alone or co-infiltrated with pBYGFP and pREP111 (abbreviated as BYGFP/REP111), whereas no green signal was found from the control infiltrated with the infiltration buffer only (FIG. 2A); in contrast, co-infiltration with BYGFP/REP110 resulted in intensive green fluorescence within the entire infiltrated area (FIG. 2A).

Similarly, N. benthamiana leaves were infiltrated with another replicon vector pBYHBc (FIG. 1) encoding the hepatitis B core antigen (HBc), a VLP-forming protein, alone or in combination with pREP110 or pREP111. HBc expression was monitored over a 7 day period by dot blotting (data not shown) and polyclonal sandwich ELISA (FIG. 3A). The BYHBc/REP110 combination had the highest expression, averaging around 0.18 mg HBc per gram fresh weight at 2 and 4 dpi. No significant difference was found between the BYHBc and the BYHBc/REP111 treatments, in agreement with the results from the GFP study.

To determine whether this increase is associated with the replicon formation, DNA extracted from infiltrated leaves was resolved in 0.8% agarose gel. A high molecular weight band representing plant chromosome DNA was observed in all samples, serving as an internal loading control. Two additional bands of ~3.0 kb and ~2.0 Kb were visualized in the BYHBc/REP110 lane, but not in the BYHBc or BYHBc/REP111 lanes (FIG. 3B). Southern blotting with HBc-specific probe confirmed that the ~3.0 kb and ~2.0 Kb bands were indeed the HBc replicons (FIG. 3B). Interestingly, digestion of plant DNA resulted in only one major band of ~3.0 kb (FIG. 3C), suggesting that the ~3.0 kb and ~2.0 kb bands represent the linear and circular forms of the replicon, respectively. Taken together, the above results demonstrate a tight correlation between replicon amplification and target protein accumulation for the BYHBc/REP, strongly suggesting that the higher protein yield is mostly due to high copy number of replicons.

A. Gene Silencing Inhibitor P19 Enhanced Accumulation of Target-Specific mRNA and Protein Gene silencing inhibitor P19 from tomato bushy stunt virus has been reported to enhance the target protein accumulation by suppressing gene silencing (Voinnet et al., 1998). To test if inclusion of P19 into the replicon system can further elevate the protein accumulation, a P19 expression vector (FIG. 1) was co-infiltrated with combinations of replicon and Rep-supplying vectors and found that BYGFP/REP110/P19 yield the most intensive GFP fluorescence (FIG. 2B). Similarly, the BYHBc/REP110/P19 combination yielded the highest HBc expression, averaging 0.8 mg/g FW (FIG. 3A). Co-delivery of P19 did not significantly affect the replicon formation as demonstrated by agarose gel electrophoresis and Southern blotting (FIGS. 3B and 3C). In contrast, Northern blot analysis showed that accumulation of HBc-specific mRNA was greatly increased by co-expression of P19 (FIG. 3D). These results indicate that P19 indeed can increase target mRNA and protein accumulation, most likely by suppressing post-transcriptional silencing of the transgene.

1. Transient Expression and VLP Formation of Norwalk Virus Capsid Protein (NVCP)

To confirm the effectiveness of this system in producing VLP vaccines, the replicon system was also tested for the transient expression of NVCP, another VLP forming antigen. FIG. 5A shows a time course study of NVCP expression with different vector combinations. The BYsNV/REP110/P19 was the best combination, yielding NVCP at levels ~0.34 mg/g FW. These results are consistent with the findings for GFP and HBc.

The integrity of NVCP was verified by Western blotting. As shown in FIG. 5B, plant-derived NVCP showed a ~58 KDa band as did the insect cell-derived NVCP standard.

BYNVCP leaf extracts were subjected to sucrose gradient sedimentation to determine the VLP assembly. As shown in FIG. 5C, purified insect cell-derived NVCP was present primarily in fractions #10, #11 and #12, as VLPs; whereas the plant-derived NVCP was detected in these three VLP fractions and also in upper fractions representing non-VLP forms.

2. The BeYDV Replicon System is Non-Competing

Figure 6:
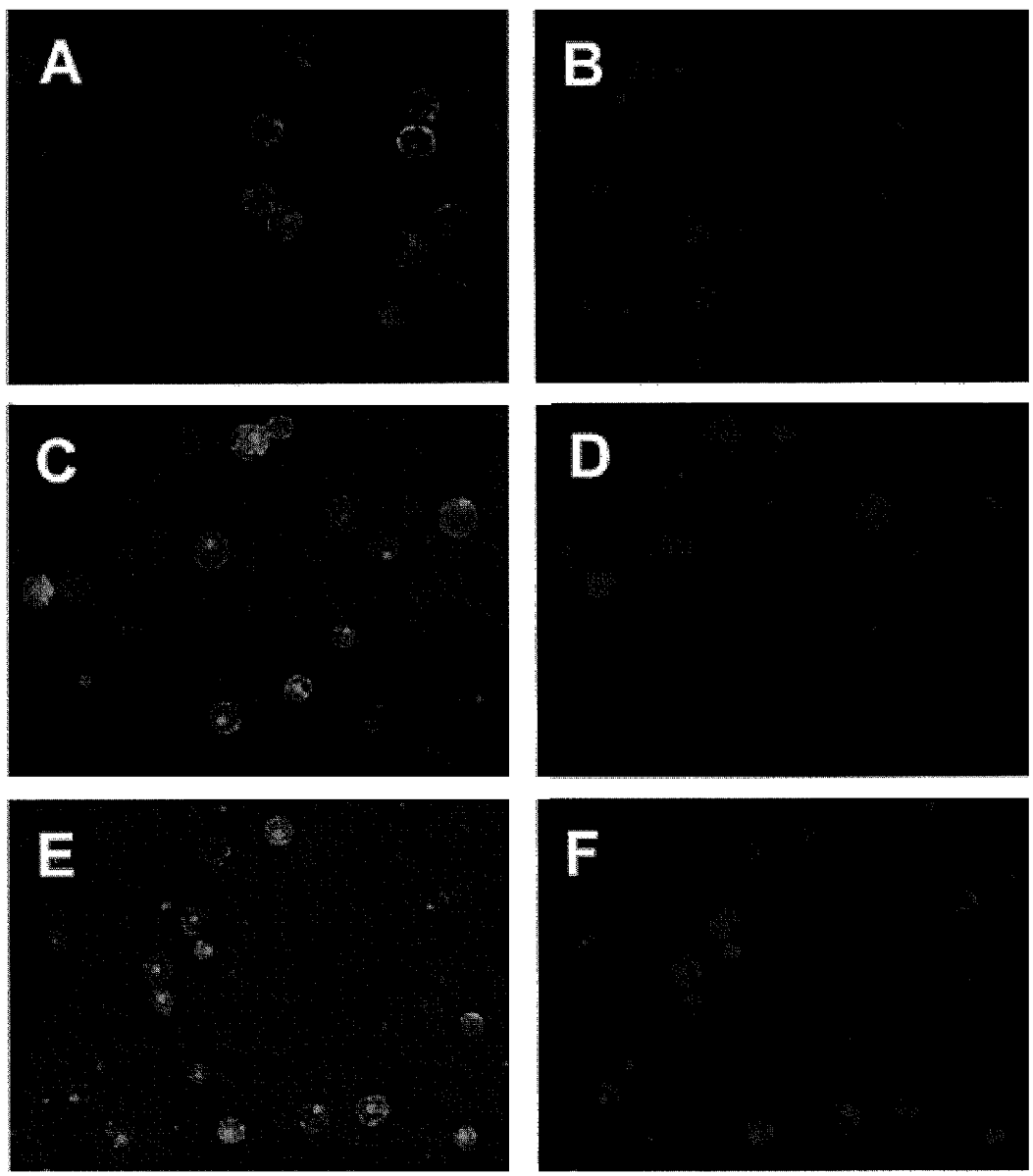
FIGS. 6A-F Fluorescence microscopy of mesophyll protoplast expressing GFP and DsRed.

Some types of VLPs, such as influenza VLPs (Latham and Galarza, 2001; Pushko et al., 2005), and therapeutics (such as mAbs, see below) containing more than one protein component, require simultaneous expression of multiple proteins within one cell. To test whether two replicons encoding different proteins can be co-expressed, N. benthamiana leaves were infiltrated with BYGFP and/or BYDsRed. Under the UV illumination, BYGFP/REP110/P19 and BYDsRed/REP110/P19 infiltrated areas displayed green and red fluorescence, respectively, while the fluorescence of BYGFP/BYDsRed co-infiltrated area appeared yellow (FIG. 2C), probably due to overlapping of both green and red fluorescence. Mesophyll protoplasts were subsequently isolated from infiltrated areas and observed under fluorescence microscope. When two populations of protoplasts that individually expressed BYGFP or BYDsRed were mixed, no overlapping fluorescent protoplast was observed (FIGS. 6A and 6B). In contrast, the majority (>80%) of the fluorescent protoplasts from co-infiltration of BYGFP/BYDsRed exhibited both green and red fluorescence (FIGS. 6C and 6D), indicating the co-expression of GFP and DsRed in the same cells. Thus, the BeYDV replicon system is non-competing, which will enable its application in producing multiple-subunit proteins such as monoclonal mAbs (see below).

Figure 9:
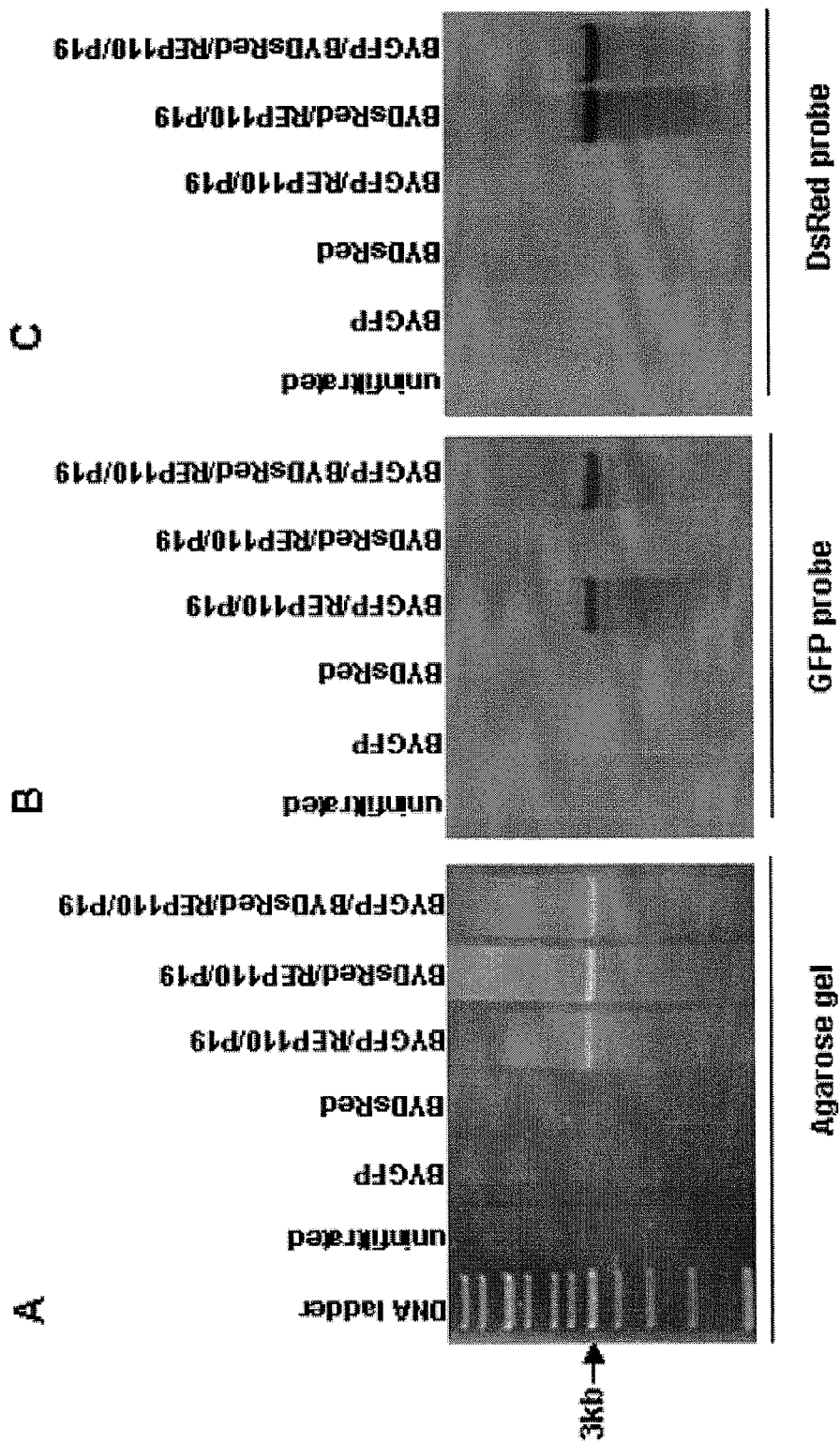
FIGS. 9A-C Southern blot analysis of non-competing formation of two replicons. Plant DNA from leaves infiltrated with vector combinations as indicated was digested with XhoI, run on 1% agarose gel (FIG. 9A), blotted onto membrane, and detected with a GFP probe (FIG. 9B) or a DsRed probe (FIG. 9C), respectively. The preparation of GFP- or DsRed-specific probes is described in Materials and Methods.

To determine whether the formation of two different replicons is not affected by the co-expression, DNA extracted from infiltrated leaves was analyzed by agarose gel and subsequent Southern blotting. As shown in FIG. 9A, no discrete band was observed for the uninfiltrated, the BYGFP alone, or the BYDsRed alone samples; in contrast, a ~3 kb band was visualized in the BYGFP/REP110/P19, the BYDsRed/REP110/P19, and the BYGFP/BYDsRed/REP110/P19 lanes, indicating efficient formation of DNA replicons. The size (~3 kb) of the bands is as expected for both BYGFP and BYDsRed replicons, as GFP and DsRed genes are of very similar length. To further verify the identity of the replicons, Southern blotting with both GFP and DsRed probes was performed. As expected, the BYGFP/REP110/P19 replicon reacted with only the GFP probe while the BYDsRed/REP110/P19 with only the DsRed probe (FIGS. 9B-C); however, the BYGFP/BYDsRed/REP110/P19 sample produced positive signals for both GFP and DsRed probes with the signal intensity similar to those representing the corresponding single replicons (FIGS. 9B-C), suggesting the BYGFP and BYDsRed replicons are near-equally co-expressed. Together, these results demonstrate that the BeYDV replicon system is non-competing, which will enable its application in producing multiple-subunit proteins of pharmaceutical importance, such as mAbs.

3. High-Yield Transient Expression of a Protective mAb Against Glycoprotein gp1 of Ebola Virus To demonstrate the versatility of the non-competing expression system, a protective mAb was expressed against Ebola virus glycoprotein gp1 (6D8) by co-infiltration of N.

benthamiana leaves with two replicon vectors, pBY-H(6D8) and pBY-L(6D8) (FIG. 1), encoding the heavy chain and light chain subunits of 6D8, respectively. The results showed that 6D8 mAb can be rapidly produced in 4-6 days post infection with expression level between 0.3-0.5 mg/g FW (FIG. 7A). The level of mAb expression is comparable to the highest level ever achieved with a plant-based expression system (Giritch et al., 2006). Western analysis confirmed the presence of both light and heavy chains (FIG. 7B, lane 3). Comparison of banding patterns on reducing and nonreducing gels indicated that the antibody is fully assembled without clipping in the light or heavy chains (FIG. 7C, lane 3). In addition to the fully assembled heterotetramer major band, minor bands corresponding to the partially assembled heterotrimer, heterodimer etc were also observed under non-reducing condition on western blot (FIG. 7C, lane 3). The ratio between the fully-assembled vs. partial assembled molecules is similar to that of the human IgG positive control and that of mAbs produced by the magnICON system (Giritch et al., 2006), indicating the assembly of the mAb is as efficient as in the current best plant transient system.

4. Single-Vector Replicon System

Figure 8:
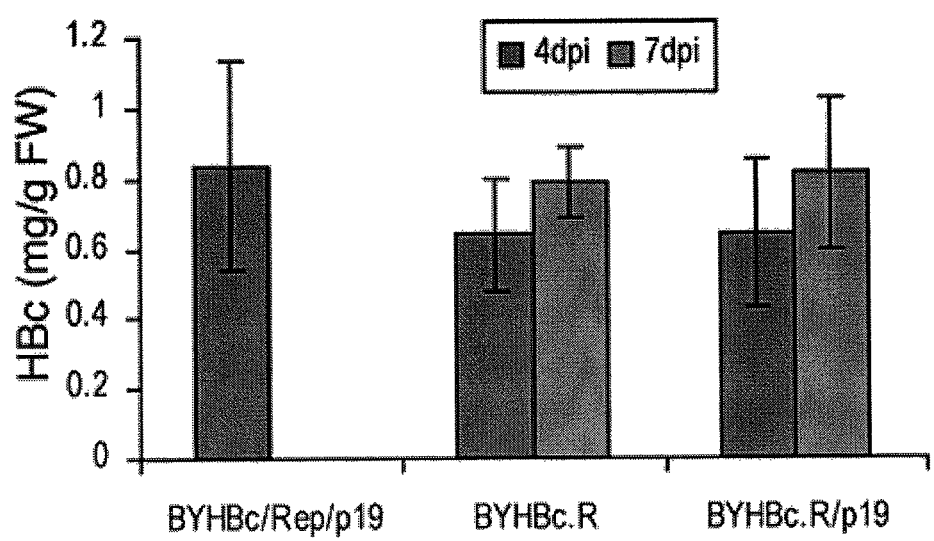
FIG. 8 Expression of HBc using a single replicon vector. Extracts from N. benthamiana leaves infiltrated with BYHBc/REP110/P19, BYHBc.R, or BYHBc.R/P19 were analyzed for HBc expression by a polyclonal ELISA. Data reported are means±S.D. from four independently infiltrated samples.

The potential to simplify the 3-vector replicon system without compromising yields was investigated. Replicon vectors containing a native C1/C2 coding region under the control of the viral LIR promoter were constructed for the expression of GFP (pBYGFP.R) and HBc (pBYHBc.R), respectively (FIG. 1). UV illumination of infiltrated leaves at 5 dpi revealed that the BYGFP.R or the BYGFP.R/P19 samples exhibited fluorescence with intensity similar to that of BYGFP/REP110/P19 but higher than that of BYGFP/REP110 (FIG. 2D). In addition, it was found that the BYHBc.R and BYHBc.R/P19 samples expressed HBc at levels comparable with those of BYHBc/REP110/P19 at 4 or 7 dpi (FIG. 8). No BYHBc/REP110/P19 sample was collected at 7 dpi due to severe necrosis. These results collectively demonstrate that the simpler single-vector replicon system is as efficient as the three-component system in terms of the final yield of protein of interest.

In order to express two target proteins using a single replicon vector, pBYGFPDsRed.R was constructed for co-expression of GFP and DsRed (FIG. 1). It was hypothesized that tandem linked replicons would be released and amplified independently, resulting in efficient expression of both proteins. Examination of protoplasts prepared from pBYGFPDsRed.R infiltrated leaves showed that both GFP and DsRed fluorescence were simultaneously detected in ~95% of the fluorescent protoplasts (FIGS. 6E and 6F). Therefore, the single replicon vector system yields high-level co-expression of multiple target proteins in the same cells.

Figure 10:
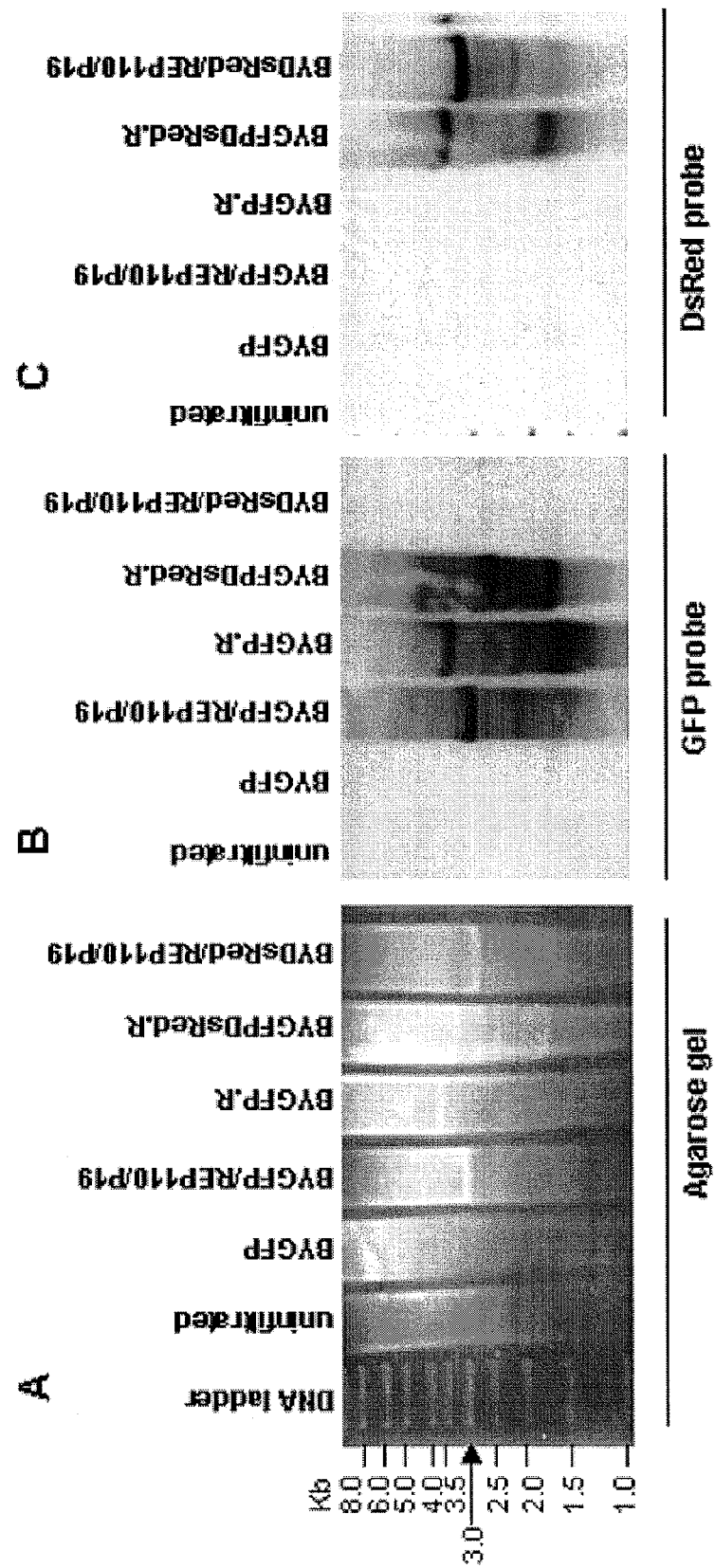
FIGS. 10A-C Formation of two separate replicons by a single vector. Plant DNA from leaves infiltrated with various vector combinations as indicated was digested with XhoI, run on 1% agarose gel (FIG. 10A), blotted onto membrane, and detected with a GFP probe (FIG. 10B) or a DsRed probe (FIG. 10C), respectively. The preparation of GFP- or DsRed-specific probes is described in Materials and Methods.

It has been shown that the three-vector replicon system can be simplified without compromising yields (Huang et al. 2009). A single vector replicon containing a native REP expression cassette (C1/C2 coding region under the control of the viral LIR promoter) (such as the BYGFP.R in FIG. 1) is as efficient as the three-vector system for the expression of single protein (Huang et al. 2009). To test if the single-vector replicon system can be used to simultaneously express multiple proteins, pBYGFPDsRed.R was constructed for co-expression of GFP and DsRed (FIG. 1). Examination of protoplasts prepared from pBYGFPDsRed.R infiltrated leaves showed that both GFP and DsRed fluorescence were simultaneously detected in ~95% of the fluorescent protoplasts (FIGS. 6E-F), indicating high-efficiency co-expression of both fluorescent proteins within same cells. Analyses of DNA from infiltrated leaves reveals the BYGFPDsRed.R sample produced replicons of different sizes which also reacted differently with GFP or DsRed probes (FIG. 10), indicating the simultaneous presence of GFP and DsRed replicons. For the BYGFPDsRed.R sample, the strongest DsRed-probe-reacting band is ~3.5 kb (FIG. 10), which is similar to the size of the BYGFP.R replicon, suggesting this band represents the DsRed replicon comprising the 35S/TEV 5'-DsRed-VSP 3'-SIR-C2/C1 sequence within the two LIRs (see FIG. 1); while the top GFP-probe-reacting band is ~2.6 kb (FIG. 10), which is expected for a smaller replicon consisting of the 35S/TMV 5'-GFP-rbcS 3'-SIR region between two adjacent LIR elements (see FIG. 1). These results demonstrate that the two tandem linked replicons can be released and amplified independently, leading to high-level proliferation of two distinct double-stranded DNA replicons and efficient expression of both proteins. Interestingly, it is also observed that in the BYGFPDsRed.R lanes a ~1.6 kb band reacted with the GFP probe and a slightly higher ~1.7 kb band less strongly with the DsRed probe (FIG. 10), probably representing the single-strand DNA form of the corresponding replicons, respectively. Nonetheless, the data indicates it is feasible to use the single replicon vector system for high-level co-expression of multiple target proteins.

B. Co-Expression and Assembly of Full-Size IgG Using a Single Replicon Vector

Figure 7:
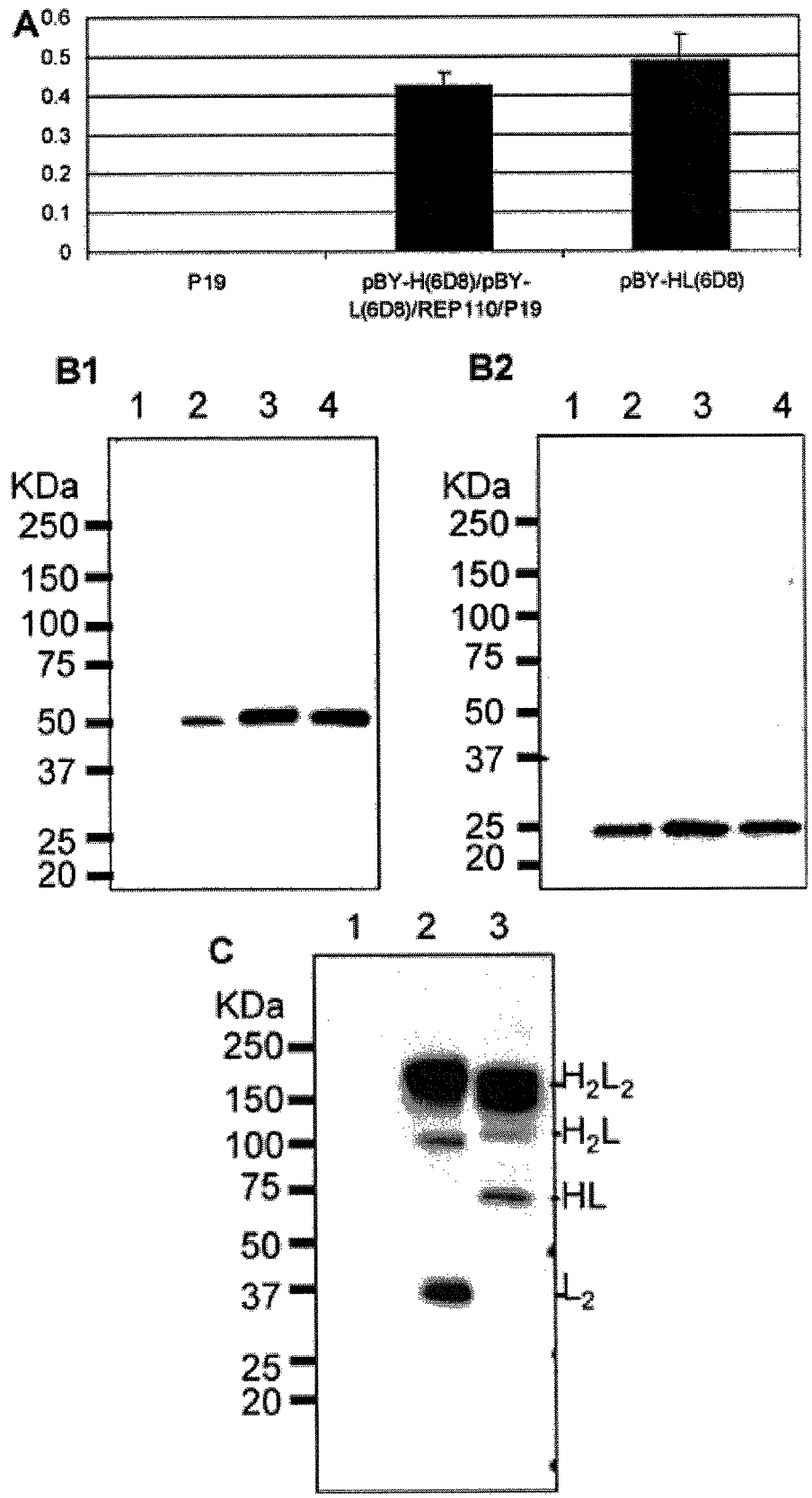
FIGS. 7A-C Characterization of a plant-derived protective mAb (6D8) against Ebola virus gp1.

To further demonstrate the effectiveness of the single-vector replicon system, a vector harboring three expression cassettes for coding sequences of the C1/C2 (Rep/RepA), the light chain and the heavy chain of a 6D8 mAb was constructed (pBY-HL(6D8).R, FIG. 1). ELISA indicated that the expression level of 6D8 by infiltration of this single-vector pBY-HL (6D8).R is comparable to (slightly higher than) that produced by the co-infiltration of four separate vectors (FIG. 7). Furthermore, SDS-PAGE and western analysis show that the mAb produced by pBY-HL(6D8).R has the correct light and heavy chain components (FIG. 7B, Lane 4) and is fully assembled as well (data not shown). These data further illustrated the potential broad-application of this simple system for making mAbs and other multiple-subunit protein pharmaceuticals.

II. Discussion

A. Development of a Single-Vector, Noncompeting Replicon Expression System

A simple plant transient expression system is not yet available for rapid high-yield production of important pharmaceuticals, especially those requiring the production and assembly of more than two distinct subunit proteins. The current study has thus been designed to address such a need. The replication mechanism of the bean yellow dwarf virus (BeYDV), a member of the geminiviruses, was exploited and ultimately developed a single-vector, replicon-based, high-yield transient expression system through a series of optimization procedures.

Geminiviruses possess single-stranded circular DNA genomes that replicate to very high-copy number in the nuclei of infected cells, making them very attractive in gene amplification strategies to increase the copy number and enhance the expression levels of foreign genes that are linked to the viral replicon (reviewed in (Palmer and Rybicki, 1998)). Mor et al. (2003) has previously showed that co-delivery of a bean yellow dwarf virus (BeYDV)-derived replicon vector and a Rep/RepA-supplying vector into tobacco NT-1 cells by bombardment resulted in replicon formation and elevated expression of target proteins. However, this process is not practically scalable. In this study, it was shown that Agrobacterium-mediated delivery of replicon vectors into plant leaf led to high-copy number replicon formation (FIG. 3) and dramatically increased target protein expression (FIGS. 3A and 5A).

Figure 3:
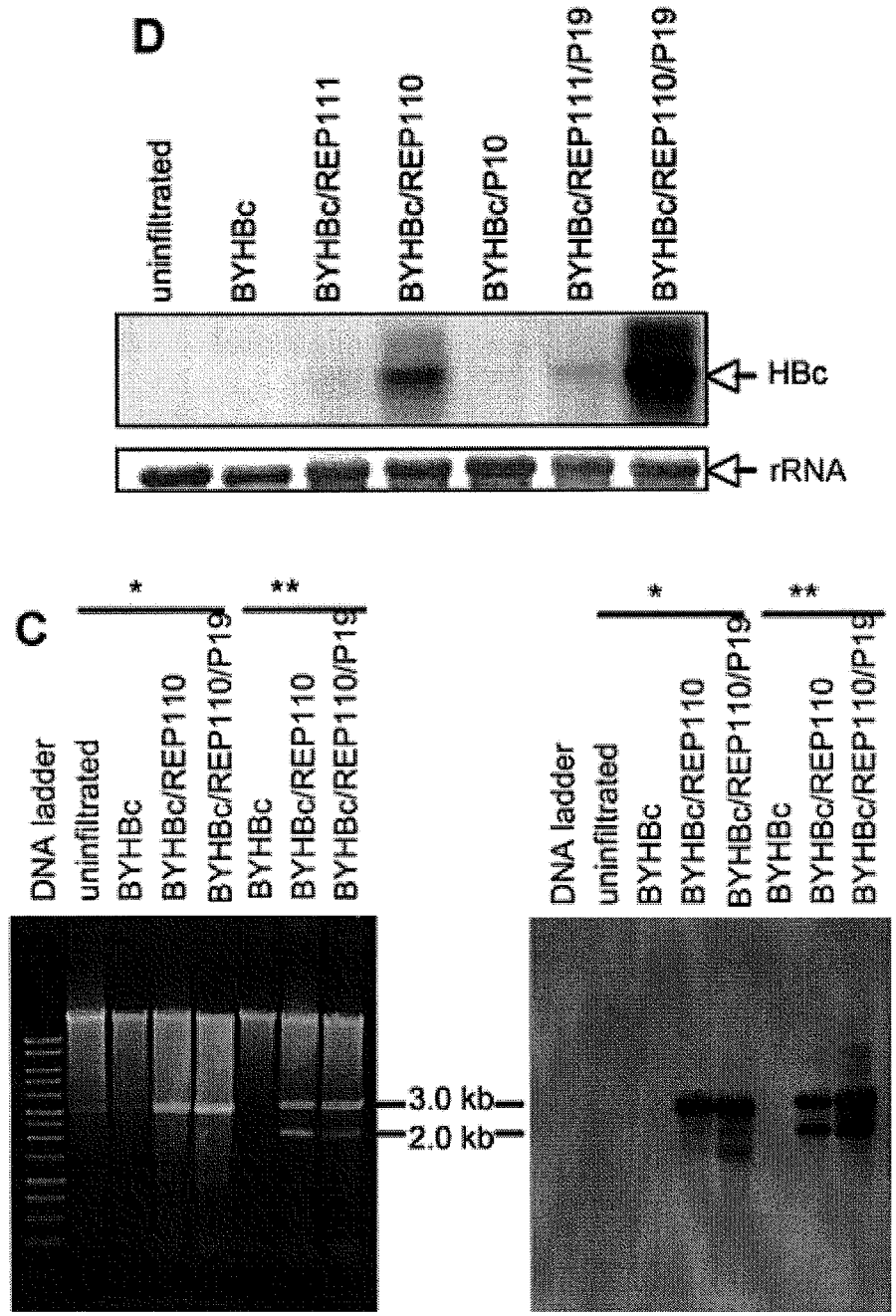
FIGS. 3A-D Transient expression of HBc in plant leaves.

Indeed, the replicon DNA is so abundant that its presence can be visualized by EtdBr staining (FIGS. 3B and 3C). The data also clearly indicate that the higher HBc yield is correlated to the high-copy numbers of replicons (FIG. 3).

In order to show the usefulness of the three-component replicon system in rapidly producing PMPs at high levels, two vaccine antigens were first tested: HBc and NVCP. Recombinant HBc and NVCP have been previously expressed in transgenic plants, however, at relatively low levels (Tsuda et al., 1998; Mason et al., 1996). For example, transgenic plants expressed up to 24 μg HBc per gram of leaf fresh weight (Tsuda et al., 1998). In contrast, the replicon system produced antigens at levels averaging 0.8 mg/g FW and 0.34 mg/g FW for HBc and NVCP respectively within 4-5 days post infection. The speed and levels of antigen accumulation are comparable to those produced by the state-of-art magnICON transient expression system (Huang et al., 2006). In addition to the results reported here, this system has successfully been used to express several other vaccine antigens, including Narita104 norovirus capsid protein and human papillomavirus L1 capsid protein (unpublished data). Overall, it was established that the geminivirus replicon system can be used to produce vaccine antigens at high levels that are suitable for future commercial development.

Until recently, it has been difficult to efficiently express heterooligomeric proteins with plant viral vectors, because co-delivery of viral vectors built on the same virus backbone always results in early segregation and subsequent preferential amplification of one of the vectors in one cell—a common scenario of "competing replicons" (Giritch et al., 2006; Dietrich and Maiss, 2003; Diveki et al., 2002; Hull and Plaskitt, 1970). This problem has been recently overcome by utilizing two sets of vectors derived from non-competing TMV and PVX, respectively (Giritch et al., 2006). However, this system requires co-infection of three construct modules per protein subunit (Giritch et al., 2006), which may present challenges when heterooligomeric proteins with more than two hetero-subunits (such as secretory IgA and IgM) are the pharmaceutical targets. As of today, there is no report of plant transient expression system that will allow efficient co-expression and assembly of heterologous proteins with more than two subunits.

Unlike traditional or "deconstructed" viral expression systems which rely on in planta assembly and replication of near-full-length viral genome, the BeYDV-derived replicon system requires only two viral elements, the LIR region and the Rep/RepA, for the initiation and amplification of episomal replicons (Mor et al., 2003). Hence, it was speculated that this system could be used for non-competing co-expression of multiple protein subunits. Indeed, co-infiltration of replicons encoding two fluorescence proteins (GFP and DsRed) resulted in the exhibition of both fluorescence, with >80% of cells co-expressing both proteins in the same cell (FIG. 6), indicating the BeYDV replicon system is noncompeting.

Monoclonal antibodies market was valued at an estimated US $14 billion, accounting for over a quarter of total protein therapeutics market (2005), and has been the fastest growing segment of the pharmaceutical industry since (Monoclonal antibodies 2007, Arrowhead publishers). Efficient production of mAbs has been a standard benchmark in evaluating the commercial feasibility of an expression system for pharmaceutical protein production. Therefore, the versatility of the replicon system was further demonstrated by producing a protective mAb against Ebola virus GP1. The results showed that the replicon system could rapidly (4 dpi) produce 6D8 mAb (FIG. 7). Furthermore, the mAb has correctly assembled into its tetrameric structure (FIG. 7C). One of the exciting results of this study is the mAb expression level is in the same range as the highest mAb level ever achieved with a plant-based expression system (FIG. 7A) (Giritch et al., 2006). In addition to 6D8, mAb-fusion proteins twice as large as 6D8 with full assembly and functionality (unpublished data) were also successfully expressed. The success in rapidly producing high-level of assembled mAb (and mAb-fusion proteins) clearly demonstrated the potential broad applications of the expression system in producing PMPs.

Knowing that the replicon system is non-competing, the focus switched to simplify the system so that it can be feasible for practical production of multiple-subunit protein pharmaceutical candidates. Specifically, the inventors wanted to determine if multiple-vector system required for expressing multiple-subunit PMPs can be simplified into a single vector without comprising yield or speed. The Rep/RepA expression cassette was first incorporated into the replicon vector. The results showed that two of such single vectors, pBYGFP.R and pBYHBc.R for expressing GFP or HBc (FIG. 1), respectively, were as efficient as their three-component counterparts in directing the expression of target proteins (FIGS. 2D and 8). In the third construct, an expression cassette for Rep, replicon for the mAb light chain and replicon for the mAb heavy chain were combined into a single vector (FIG. 1). Remarkably, infection of this single vector pBY-HL(6D8).R produced fully assembled mAb at similar levels as those produced by co-infection of four separate vectors (FIG. 7). The results from above three selected protein targets collectively show that the multiple component replicon system can be successfully simplified into a simpler single-vector system without sacrifice the final yield of target PMPs. Moreover, the success in producing the fully-assembled tetrameric IgG (two heterooligomeric subunits) with a single replicon vector strongly suggest that simultaneous expression of as many as four hetero-subunits can be easily achieved using two replicon vectors, or by creating single vectors with three or more tandem linked replicons. To the best knowledge, this technology is so far, among all plant transient expression systems, the first and the only one that has such a potential.

While the expression levels of VLP vaccines and mAb by the system are comparable to those of the best plant transient system, it is, however, not in any sense, fully optimized. There are still many genetic and technical components of this system yet to be improved. For example, anti-silencing element P19 could be incorporated into the simplified single vector system. Furthermore, the geminivirus vectors could be deconstructed to achieve better expression as for the viral elements in the magICON system (Marillonnet et al., 2004). As suggested by others, chaperones could also be included in the expression cassette to accommodate the increasing assembly demand by the high-level accumulation of oligomeric PMPs (Nuttall et al., 2002).

B. VLP Assembly

Figure 4:
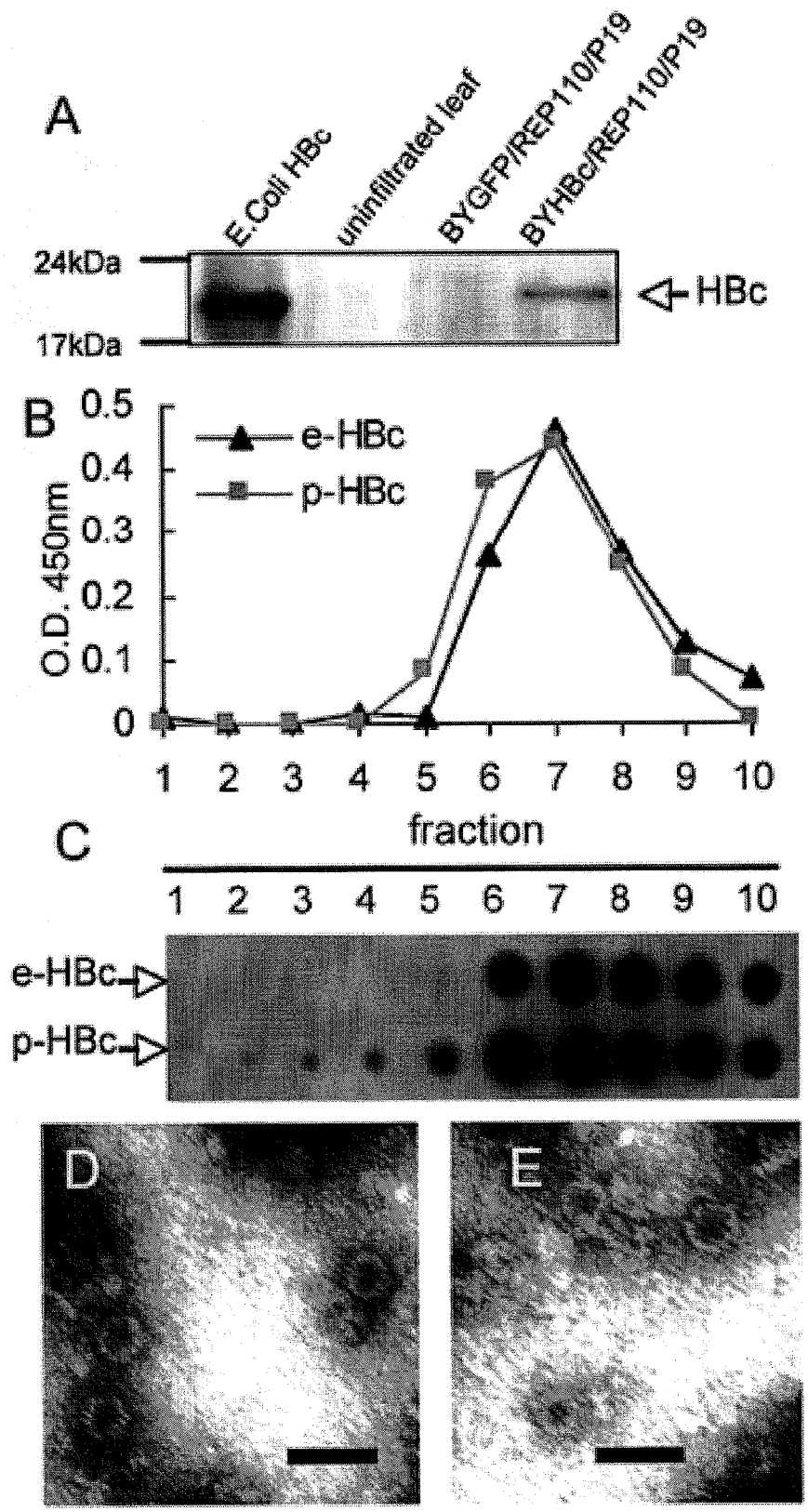
FIGS. 4A-E Characterization of plant-expressed HBc.
Figure 5:
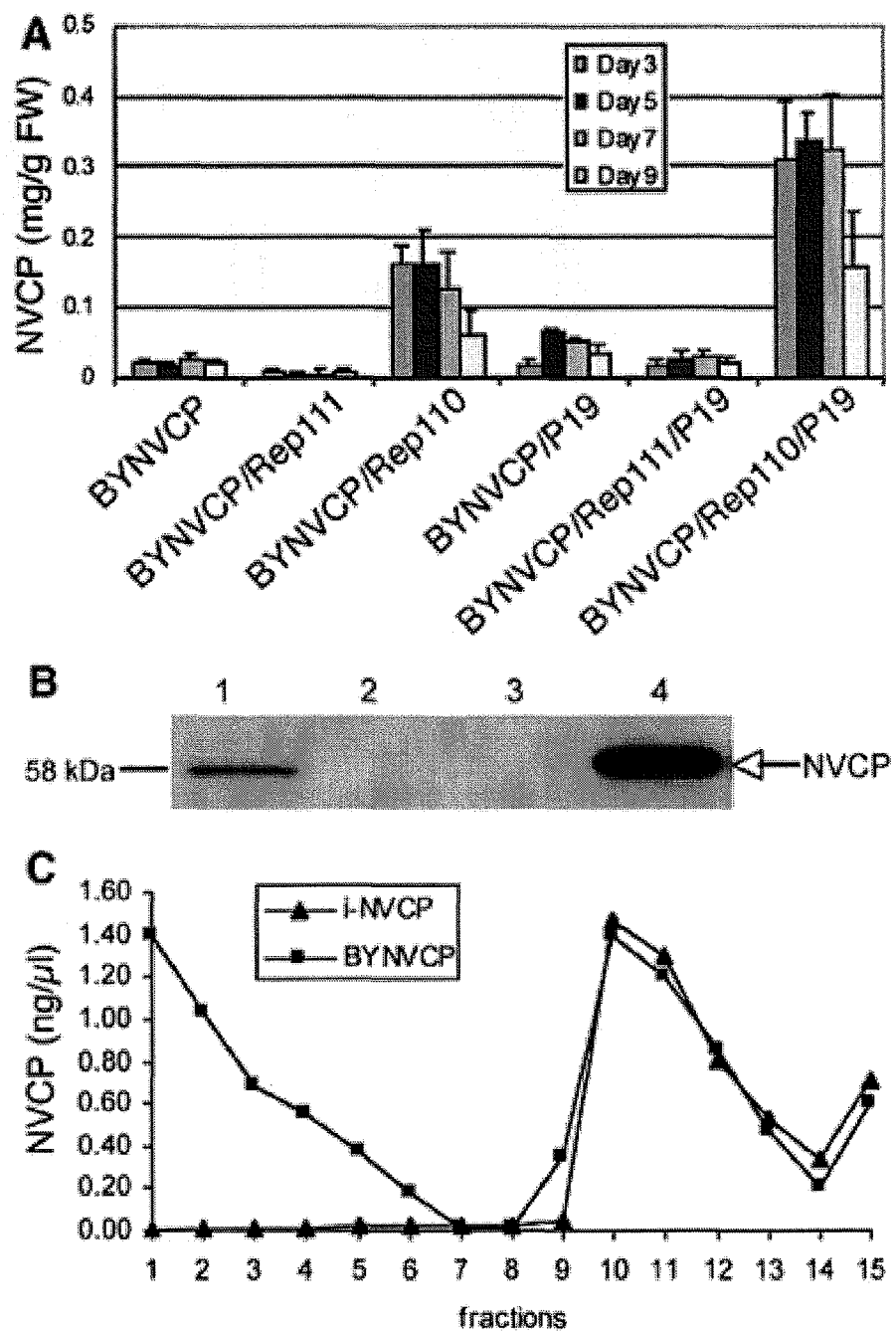
FIGS. 5A-C Transient expression of NVCP using replicon vectors.

A number of viral structural proteins can self-assemble into organized macromolecular structures termed virus-like particle (VLP), which morphologically mimics authentic virions but lacks of infectious viral genome. VLPs are very immunogenic and can be used as vaccines, especially as a safer alternative to attenuated live or inactivated virus-based vaccines (Garcea and Gissmann, 2004). For example, yeast-produced HBsAg VLP constitutes the first recombinant subunit vaccine in history (McAleer et al., 1984). In this paper, it was examined if the replicon system produced HBc and NVCP assembled into VLPs. For HBc, affirmative results were obtained by sucrose gradient analysis, ELISA, dot blot analysis, and electron microscopy (FIG. 4 and FIG. 5). Using gradient separation of proteins in NVCP crude extract, two peaks were detected on sucrose gradients which were assigned as partially assembled subunits (Top fractions, FIG. 5) and assembled VLPs (Fractions 10-12, FIG. 5). The latter peak co-migrated with VLPs produced in insect cells (FIG. 5). This "two-peaks" pattern is similar to that observed for the magnICON system produced NVCP, which was very immunogenic in mice (Santi et al., 2008). Thus, it was concluded that VLP-forming antigens produced by this replicon system can effectively assemble into high-order oligomeric VLPs.

C. Application of the Replicon Vectors in Transgenic Plant Expression Systems

As discussed in (Arntzen et al., 2005), there have been two dominate strategies for the expression of antigens in plants—stable transgenic gene expression and transient expression with viral vectors. While transient expression systems such as the one presented here provide a speedy solution to provide material for initial characterization, stable transgenic plants hold the most promising scalability when extraordinarily large amount of PMP production is needed. For both the stable and transient systems, mRNA accumulation is a bottleneck in protein expression. However, the stable transgenic technology is further complicated by the "position effect"—the mRNA level depends on the position in which the transgene inserted in the chromosome (Matzke and Matzke, 1998). As a result, finding a highly-expressing transgenic line becomes a statistical exercise, in which hundreds or even thousands of plants must be screened to identify outliers expressing at high levels. The unique nicking function of the Rep protein of geminiviruses (Laufs et al., 1995a; Laufs et al., 1995b) allows for replicative release of recombinant viral DNA cloned between a tandem repeat of the LIR from a chromosome-integrated site (Hayes et al., 1988; Grimsley et al., 1987; Kanevski et al., 1992). The DNA then replicates episomally in the nucleus. These characteristics of geminivirus replicons will enable us to develop stable transgenic vectors in which the episomal replication nature and high copy number of geminivirus replicons would eliminate position effect of transgene expression, as well as ensure a high target protein expression level in stable transformed plants. The previous study has indeed shown that an earlier version the Bean Yellow Dwarf Virus derived vector and co-expressed with Rep driven by an inducible promoter in stable transgenic potato produced an 80-fold increase in mRNA and a 10-fold increase in transgenic protein expression (Zhang and Mason, 2006). This evidence further supports the likelihood of success in using the current improved version of replicons to develop high-expressing stable transgenic vectors for large-scale PMP production. The utilization of the advanced replicon vectors in both transient and stable transgenic technologies will thus allow a rapid assessment of pharmaceutical candidates and a scalable platform for commercial production.

Overall, this research has developed a robust geminivirus-based expression system which is capable of achieving rapid high-level PMP accumulation for a broad spectrum of PMPs including VLP vaccines and multiple-subunit therapeutics. The ability of a simplified single vector to deliver multiple expression cassettes/replicons for production of mAbs and other hetero-ologimeric pharmaceuticals provides a key advantage over other systems in its commercial production feasibility. Furthermore, this system can also be applied to stable transgenic technology for large-scale PMP production. Once optimized and implemented at commercial scale, this expression system has the potential to provide a technology platform to produce pharmaceutical proteins with speed, efficiency, cost-effectiveness and safety.

Example 2

Expression of Recombinant Immune Complex (RIC)

This example illustrates the use of the tandem dual geminiviral replicon system to express a 2.87 kb gene to produce a 130 kDa protein: a modified immunoglobulin in which the gene encoding the heavy chain of monoclonal antibody 6D8 (Example 1, Results 4. Single-vector replicon system) is fused to Ebola virus glycoprotein GP1 (H2gpKDEL). Previous studies with tobacco mosaic (RNA) virus vectors showed limitations in the size of RNA molecules that could be expressed and translated to produce high molecular weight proteins. For example, the magnifection system can express genes up to 2.3 kb or up to 80 kDa protein (Gleba et al., 2007). Moreover, the current example demonstrates the co-expression of the heavy chain fusion H2gpKDEL and the light chain K3 in separate geminiviral replicons contained in the same T-DNA plasmid.

The construct pBYR-H2gpKDEL-K3 is analogous to and derived from pBY-HL (6D8).R described in Example 1 (Results 4. Single-vector replicon system). To construct pBYR-H2gpKDEL-K3, a 1407-bp plant-optimized gene encoding the Ebola virus (Zaire strain, Genbank AY354458) GP1 with a C-terminal addition of the hexapeptide SEKDEL was fused to the C-terminus of the humanized 6D8 H2 heavy chain via a linker $(G_4S)_3$, essentially as described (Chargelegue et al., 2005). The heavy chain fusion (H2gpKDEL) was ligated into pBY-HL(6D8).R in place of the 6D8 heavy chain, to give the dual replicon construct pBYR-H2gpKDEL-K3. This T-DNA plasmid was electroporated into *Agrobacterium tumefaciens* LBA4404, and confirmed by plasmid preparation and restriction digests.

The *Agrobacterium* culture at $O.D._{600}$=0.25 was mixed with an equal volume of Agrobaceria harboring the P19 construct (Example 1) at $O.D._{600}$=0.25 and vacuum-infiltrated into leaves of whole *Nicotiana benthamiana* plants that were 4-5 weeks old. Leaves were harvested 4 days later and extracted as described in Example 1 using extraction buffer containing PBS (pH 7.5) and protease inhibitor tablet (Sigma Chemicals). The cleared supernatant (10,000 g) was then subjected to ammonium sulfate fractionation, with the RIC obtained in the 35-60% fraction. The RIC fraction was then subjected to protein G affinity chromatography (Pierce Protein Research Products) as described in the product literature.

Figure 11:
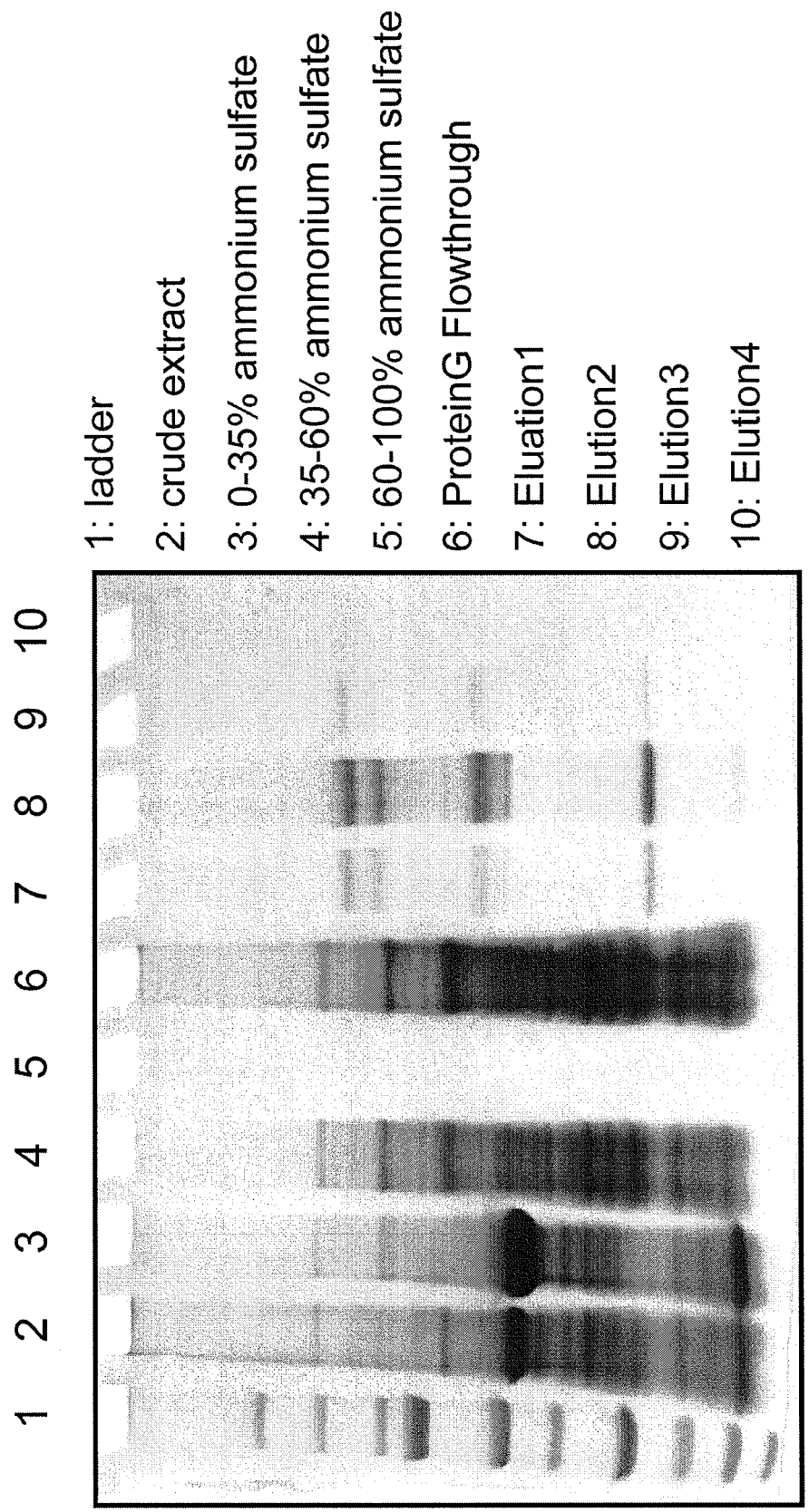
FIG. 11 pBYR-H2gpKDEL-K3 expression products in leaves analyzed by reducing SDS-PAGE and stained with Coomassie blue. Lanes 3, 4, and 5 show leaf proteins precipitated by ammonium sulfate solutions at 0-35%, 35-60%, and 60-100% saturated solutions, respectively. The 35-60% fraction was subjected to protein G affinity chromatography: lane 6, flow-through (unbound); lanes 7, 8, 9, 10 are sequential elutions of bound material.

FIG. 11 shows the results of purification steps by reducing SDS-PAGE analysis. The ammonium sulfate fractionation removed the great majority of RuBP carboxylase, and protein G affinity yielded highly purified heavy and light chains, along with some apparent proteolytic products (lanes 7, 8, 9).

Figure 12:
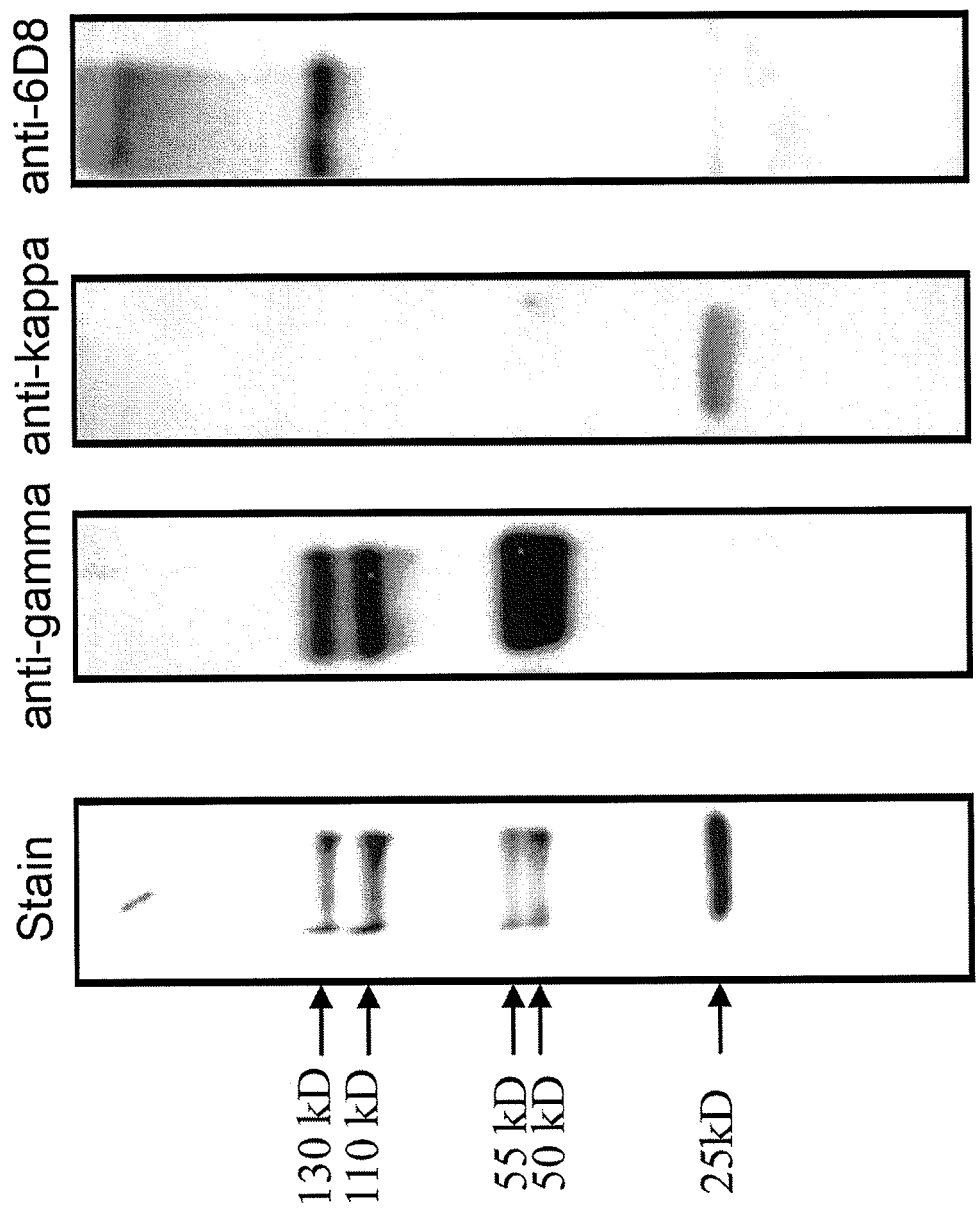
FIG. 12 Protein G affinity purified leaf extracts analyzed by reducing SDS-PAGE and Western blots. Stain, proteins stained with Coomassie blue; anti-gamma, Western blot probed with anti-human gamma chain; anti-kappa, Western blot probed with anti-human kappa chain; anti-6D8, Western blot probed with anti-GP1 (6D8 mouse monoclonal antibody).

FIG. 12 shows the purified RIC analyzed by reducing SDS-PAGE and western blots. Probes for anti-human gamma chain and anti-GP1 (6D8 epitope) detected a band at 130 kDa, the expected full-length H2gpKDEL fusion. In addition, the anti-gamma chain probe detected 3 other bands at 110, 55, and 50 kDa, likely representing proteolytic products of the full-length fusion protein. The kappa chain probe showed the expected 25-kDa protein. Thus, both the heavy chain fusion (H2gpKDEL) and the light chain were expressed and accumulated using the dual replicon vector pBYR-H2gpKDEL-K3. A practical limit to the length of coding sequence that can be expressed with this system has yet to be found.

Example 3

Methods

Vector construction. A plasmid pBY036 containing the native BeYDV C1/C2 genes between the 35S promoter/TEV 5' UTR and the VSP terminator was described previously (Mor et al., 2003). The C1/C2 expression cassette was released from pBY036 by XhoI/SacI digestion and inserted into pPS1 (Huang and Mason, 2004) from the same site, making binary vector pREP110 for expression of both Rep and RepA (FIG. 1). The binary vector pREP111 was similarly generated from pBY037 (Mor et al., 2003) for expression of Rep only. The P19 gene from tomato bushy stunt virus was amplified from pTBSV (H. Scholthof, Texas A&M University) using primers P19-Bam (5'-tcaaggatccatggaacgagc-tataca) (SEQ ID NO:1) and P19-Sac (5'-agaggagctatactcgc-cttctttttc) (SEQ ID NO:2), digested with NcoI and SacI and inserted in pPS1, yielding binary vector pPSP19.

Replicon vectors were constructed based on backbone vector pBY023 (Mor et al., 2003). The NVCP replicon in pBYsNV410 (Zhang and Mason, 2006) was released by digestion with AscI and FseI and ligated with pBY023 at the same sites to make pBYNVCP. The GFP gene was amplified from pICH7410 (Marillonnet et al., 2004) (Icon Genetics) using primers P-GFP/NcoI.F (5-GTCACCATGGTGAG-CAAGGGCGAG) (SEQ ID NO:3) and P-GFP/SacI.R (5'-ATTAGAGCTCTTACTTGTACAGCTCGTC) (SEQ ID NO:4), digested with NcoI and SacI, and inserted into pIBT210 (Haq et al., 1995) to make pGFPi210. The XhoI-SacI fragment containing TEV 5'UTR-GFP was ligated into the same sites of pBYsNV110 (Zhang et al., 2006) to make pBYGFP. The DsRed gene was amplified from pDsRed1-1 (Clontech cat #6922-1) with primers 5'-ATCGTCTAGAAC-CATGGTGCGCTCCTCCAAG (SEQ ID NO:5) and 5'-ATTAGAGCTCCTACAGGAACAGGTGGTG (SEQ ID NO:6), digested with XbaI and SacI, and ligated into pIBT210 to make pIBT-DsRed, from which the XhoI-SacI fragment was substituted into pBYGFP to make pBYDsRed. The hepatitis B core antigen gene (HBc) was obtained from pICH-HBc (Huang et al., 2006) by digestion with NcoI-SacI, ligated into pIBT210, and then subcloned via XhoI-SacI into pBYGFP to make pBYHBc. Rep gene-containing replicons were made by insertion of the 727 by BamHI fragment of BeYDV C1/C2 gene from pBY002 (Mor et al., 2003) into pBYGFP and pBYHBc to make pBYGFP.R and pBYHBc.R, respectively.

Tandem dual replicon constructs used CaMV 35S promoters with a single enhancer element, obtained by amplification of the expression cassettes in pBYDsRed and pIBT210.3 (Judge et al., 2004) with primers 35S-Sda (5'-TGACCTG-CAGgCATGGTGGAGCACGACA) (SEQ ID NO:7) and VSPHT (5'-TGAATAGTGCATATCAGCATACCTTA) (SEQ ID NO:8). The promoter and 5'-UTR of tobacco mosaic virus (TMV) in the fragment amplified from pIBT210.3, the GFP gene from pBYGFP, and the pea ribulose1,5-bisphosphate carboxylase small subunit (rbcS) terminator (Friedrichsen et al., 2000) were ligated together into the PstI and EcoRI sites of pBY024 (Mor et al., 2003) to make pBYGFP210.3. The fragment containing the GFP replicon, obtained by digestion of pBYGFP210.3 with BamHI, filling with Klenow enzyme, and then AscI, was ligated with the 35S-Sda amplified pBYDsRed replicon digested with AscI, filled with Klenow enzyme, and then SacI, into the vector pBYHBc.R that had been digested with AscI and SacI, to make pBY-GFPD-sRed.R.

The gene sequences for heavy (H2) and light (K3) chains of mouse monoclonal antibody 6D8 (Wilson et al., 2000) were de-immunized for humans by substitution of human constant region sequences for gamma type 1 and kappa chains (Biovation, Edinburgh, Scotland). The resulting sequences were used to design plant codon-optimized genes, and synthesized commercially (Retrogen, San Diego, Calif.). The H2 gene in pCHF4-6D8-H2 (Mapp Biopharmaceutical, Inc.) was end-tailored to add a C-terminal 'SEKDEL' hexapeptide by PCR with the primer H2-SEKDEL-Kpn (5'-GCGGTACCT-TAAAGCTCATCCTTCTCTGATTTACCCG-GAGACAAGGAGAG) (SEQ ID NO:9), digested with NcoI and KpnI, and inserted into pPS1 to make p6D8-H2, from which the XhoI-EcoRI fragment containing TEV5'-UTR-H2-VSP3' was substituted into pBYGFP to make pBYH (6D8). The K3 gene in pCHF4-6D8-K3 (Mapp Biopharmaceutical, Inc.) was obtained as an NcoI-KpnI fragment, ligated with the 35S promoter-TMV5' and the rbcS3' elements, and substituted thus into pBYGFP vector to make pBY-L(6D8). The replicon (LIR to SIR) from pBY-L(6D8) was substituted into pBYGFP.R to make pBYK3 R. The H2-SEKDEL fragment was amplified from pBY-H(6D8) with primers H2-Xba (5'-ACGATCTAGAACAATGG-GATGGTCTTGCATC) (SEQ ID NO:10) and VSPHT, digested with XbaI and KpnI, and substituted into the vector pBY027 (Mor et al., 2003) to make pBY-H2K210. The replicon from pBY-H2K210 was then inserted into pBYK3R to make the tandem dual replicon construct pBY-HL(6D8).R.

Agroinfiltration procedure. Binary vectors were separately introduced into *Agrobacterium tumefaciens* LBA4404 by electroporation. The resulting strains were verified by restriction digest of plasmids, grown overnight at 30° C. and used to infiltrate leaves of 6 to 8 week-old greenhouse-grown Nicotiana benthamiana plants. Briefly, the bacteria were pelleted by centrifugation for 5 min at 5,000×g and then resuspended in infiltration buffer (10 mM 2-(N-morpholino)ethanesulfonic acid (MES), pH5.5 and 10 mM $MgSO_4$) to desired optical density (OD) at 600 nm. The resulting bacterial suspensions were injected by using a syringe without needle, either alone or as a mixture of several strains, into fully expanded leaves through a small puncture (Huang and Mason, 2004).

Plant DNA extraction and Southern blotting. Total DNA from plant leaves was extracted as described (Zhang and Mason, 2006). DNA (~3 μg) was either undigested or digested with Xho I, resolved in 0.8% agarose gel, stained with ethidium bromide, transferred to a nylon membrane (Zeta-probe, Bio-Rad, Hercules, Calif.). Membranes were then hybridized with a digoxygenin (DIG)-labeled HBc-specific probe, which was synthesized by PCR with primers anchored to 5' (-TAGCCATGGACATTGACCCTT-) (SEQ ID NO:11) and 3' (-TTAACATTGAGATTCCCT-) (SEQ ID NO:12) ends of the HBc gene, respectively, according to manufacturer's instructions (Roche Applied Science, Indianapolis, Ind.).

Plant RNA extraction and Northern blotting. Total RNA isolation and RNA blot analysis were performed as described (Zhang and Mason, 2006). The transcripts of HBc were detected using DIG-labeled probes prepared as for DNA blots.

Protein analysis. For HBc analysis, total soluble protein from *N. benthamiana* leaf was extracted and measured as previously described (Huang et al., 2005). Total HBc was quantified by a sandwich ELISA as previously described (Huang et al., 2006) with slight modification: a mouse polyclonal anti-HBc [*E. coli*-derived recombinant HBc (ViroGen, Watertown, Mass.) injected i.p.] diluted 1:5,000 was used for detection. Dot blotting, Western blotting and sucrose gradient sedimentation were performed as previously described (Huang et al., 2006).

For NVCP analysis, total leaf protein was extracted with ice-cold acid extraction buffer (25 mM sodium phosphate buffer, pH 5.75, 100 mM NaCl, 50 mM sodium ascorbate and 10 µg/ml leupeptin) using a FastPrep machine, and cleared supernatants were assayed for NVCP by ELISA as described (Mason et al., 1996). Western blotting was performed as previously described (Mason et al., 1996) except probing with a rabbit anti-rNV serum. Sucrose gradient sedimentation of NVCP extracts followed a modified protocol (Mason et al., 1996). Briefly, plant extracts or insect cell-derived NVCP standard were layered onto linear 5 ml 10-60% sucrose gradients dissolved in modified phosphate buffer (25 mM sodium phosphate, pH 5.75, 100 mM NaCl). After centrifugation in a Beckman SW55Ti rotor at 45,000 rpm for 3 h at 4° C., 15 fractions (0.333 ml each) were taken and assayed for NVCP content by ELISA.

For 6D8 mAb analysis, total leave protein was extracted with extraction buffer (25 mM sodium phosphate, pH 6.6, 100 mM NaCl, 1 mM EDTA, 0.1% Triton X-100, 10 mg/ml sodium ascorbate, 10 µg/ml leupeptin, 0.3 mg/ml phenylmethylsulfonyl fluoride) using a FastPrep machine (Bio101). The clarified total protein extract was analyzed with ELISA which was designed to detect the assembled form of mAb (with both light and heavy chain) as described previously (Giritch et al., 2006). Specifically, plates were coated with a goat anti-human IgG specific to gamma heavy chain (Southern Biotech). After incubation with plant protein extract, a HRP-conjugated anti-human-kappa chain antibody (Southern Biotech) was used as the detection antibody. The gamma and kappa specific antibodies above were also used for western blot analysis.

Electron microscopy. HBc was partially purified from infiltrated leaves as previously described (Huang et al., 2006). Partially purified HBc was subjected to negative staining with 0.5% aqueous uranyl acetate, and transmission electron microscopy was performed with a Philips CM-12S microscope.

Isolation of N. benthamiana mesophyll protoplasts. Protoplasts were released from infiltrated leaf tissue by incubation for 10-16 hours at room temperature in a solution containing 0.4M mannitol, 8 mM $CaCl_2$, 0.4% cellulase and 0.4% Macerozyme R-10. Released protoplasts were filtrated through a nylon mesh with a 62-µm pore diameter.

Visualization of GFP and DsRed. Leaves expressing GFP were viewed under UV illumination generated by a B-100AP lamp (UVP, Upland, Calif.). Leaves co-expressing GFP and DsRed were viewed under a UVGL-25 lamp (UVP, Upland, Calif.). Protoplasts were viewed with a Nikon inverted microscope with GFP filter sets (Chroma #41028; excitation filter, 500/20 nm; emission filter, 535/30 nm) and DsRed filter sets (Chroma #42005; excitation filter, 540/40 nm; emission filter, 600/50 nm).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,338,298
U.S. Pat. No. 4,366,241
U.S. Pat. No. 4,659,774
U.S. Pat. No. 4,682,195
U.S. Pat. No. 4,683,195
U.S. Pat. No. 4,683,202
U.S. Pat. No. 4,684,611
U.S. Pat. No. 4,748,018
U.S. Pat. No. 4,800,159
U.S. Pat. No. 4,816,571
U.S. Pat. No. 4,879,236
U.S. Pat. No. 4,883,750
U.S. Pat. No. 4,952,500
U.S. Pat. No. 4,959,463
U.S. Pat. No. 5,141,813
U.S. Pat. No. 5,264,566
U.S. Pat. No. 5,279,721
U.S. Pat. No. 5,302,523
U.S. Pat. No. 5,322,783
U.S. Pat. No. 5,384,253
U.S. Pat. No. 5,428,148
U.S. Pat. No. 5,464,765
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,554,744
U.S. Pat. No. 5,563,055
U.S. Pat. No. 5,574,146
U.S. Pat. No. 5,580,859
U.S. Pat. No. 5,589,466
U.S. Pat. No. 5,591,616
U.S. Pat. No. 5,602,244
U.S. Pat. No. 5,610,042
U.S. Pat. No. 5,645,897
U.S. Pat. No. 5,656,610
U.S. Pat. No. 5,702,932
U.S. Pat. No. 5,705,629
U.S. Pat. No. 5,736,524
U.S. Pat. No. 5,780,448
U.S. Pat. No. 5,789,215
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717

U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,871,986
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,565
U.S. Pat. No. 5,928,862
U.S. Pat. No. 5,928,869
U.S. Pat. No. 5,928,905
U.S. Pat. No. 5,928,906
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 6,756,361
U.S. Pat. No. 6,770,278
U.S. Pat. No. 6,936,258
Abbondanzo et al., *Breast Cancer Res. Treat.*, 16:182(151), 1990.
Allred et al., *Arch. Surg.*, 125(1):107-113, 1990.
Almendro et al., *J. Immunol.*, 157(12):5411-5421, 1996.
Arntzen et al., *Vaccine*, 23:1753-1756, 2005.
Ausubel et al., In: *Current Protocols in Molecular Biology*, John, Wiley & Sons, Inc, New York, 1996.
Ausubel et al., In: *Current Protocols in Molecular Biology*, John, Wiley & Sons, Inc, New York, 1989.
Baichwal and Sugden, In: *Gene Transfer*, Kucherlapati (Ed.), Plenum Press, NY, 117-148, 1986.
Bellus, *J. Macromol. Sci. Pure Appl. Chem.*, A31(1): 1355-1376, 1994.
Borrebaeck, In: *Antibody Engineering—A Practical Guide*, W. H. Freeman and Co., 1992.
Brown et al., *Immunol Ser*, 53:69-82, 1990.
Burke et al., *J. Inf. Dis.*, 170:1110-1119, 1994.
Canizares et al., *Immunol. Cell. Biol.*, 83:263-270, 2005.
Capaldi et al., *Biochem. Biophys. Res. Comm.*, 74(2):425-433, 1977.
Carbonelli et al., *FEMS Microbiol. Lett.*, 177(1):75-82, 1999.
Chandler et al., *Proc. Natl. Acad. Sci. USA*, 94(8):3596-601, 1997.
Chargelegue et al., *Infection and Immunity*, 73(9), 5915-5922, 2005.
Chen and Okayama, *Mol. Cell Biol.*, 7(8):2745-2752, 1987.
Cocea, *Biotechniques*, 23(5):814-816, 1997.
Coupar et al., *Gene*, 68:1-10, 1988.
De Jager et al., *Semin. Nucl. Med.*, 23(2):165-179, 1993.
Dietrich and Maiss, *J. Gen. Virol.*, 84:2871-2876, 2003.
Diveki et al., *Biochimie.*, 84:997-1002, 2002.
Doolittle and Ben-Zeev, *Methods Mol, Biol*, 109:215-237, 1999.
EP 266,032
EPA 320 308
EPA 329 822
Epitope Mapping Protocols, 1996.
Fechheimer et al., *Proc Natl. Acad. Sci. USA*, 84:8463-8467, 1987.
Floss et al., *Transgenic. Res.*, 16:315-332, 2007.
Fraley et al., *Proc. Natl. Acad. Sci. USA*, 76:3348-3352, 1979.
Friedmann, *Science*, 244:1275-1281, 1989.
Friedrichsen et al., *Plant Physiol.*, 123:1247-1256, 2000.
Froehler et al., *Nucleic Acids Res.*, 14(13):5399-5407, 1986.
Frohman, In: *PCR Protocols: A Guide To Methods And Applications*, Academic Press, N.Y., 1990.
Garcea and Gissmann, *Curr. Opin. Biotechnol.*, 15:513-517, 2004.
GB Appn. 2 202 328
Giddings et al., *Nat. Biotechnol.*, 18:1151-1155, 2000.
Giddings, *Curr. Opin. Biotechnol.*, 12:450-454, 2001.
Giritch et al., *Proc. Natl. Acad. Sci. USA*, 103:14701-14706, 2006.
Gleba et al., *Curr Opin. Biotechnol.*, 18(2):134-141, 2007.
Gopal, *Mol. Cell Biol.*, 5:1188-1190, 1985.
Graham and Van Der Eb, *Virology*, 52:456-467, 1973.
Grimsley et al., *Nature*, 325:177-179, 1987.
Gulbis and Galand, *Hum. Pathol.*, 24(12):1271-1285, 1993.
Hanley-Bowdoin et al., *Cri. Rev. Plant Sci.*, 18:71, 1999.
Hanley-Bowdoin et al., *Proc. Natl. Acad. Sci. USA*, 87(4):1446-1450, 1990.
Haq et al., *Science*, 268:714-716, 1995.
Harland and Weintraub, *J. Cell Biol.*, 101(3):1094-1099, 1985.
Harlow and Lane, In: *Antibodies: A Laboratory Manual*, Cold Spring Harbor Laboratory, 1988.
Hayes et al., *Nature*, 334:179-182, 1988.
Hermonat and Muzycska, *Proc. Natl. Acad. Sci. USA*, 81:6466-6470, 1984.
Hood et al., *Curr. Opin. Biotechnol.*, 13:630-635, 2002.
Horwich et al. *J. Virol.*, 64:642-650, 1990.
Huang and Mason, *Plant Biotechnol. J.*, 2:241-249, 2004.
Huang et al. *Biotechnol. Bioeng.*, 103(4):706-714, 2009.
Huang et al., *Vaccine*, 23:1851-1858, 2005.
Huang et al., *Vaccine*, 24:2506-2513, 2006.
Hull and Plaskitt, *Virology*, 42:773-776, 1970.
Huston et al., In: *Methods in Enzymology*, Langone (Ed.), Academic Press, NY, 203:46-88, 1991
Innis et al., *Proc. Natl. Acad. Sci. USA*, 85(24):9436-9440, 1988.

Inouye and Inouye, *Nucleic Acids Res.*, 13:3101-3109, 1985.
Johnson et al., *Methods in Enzymol.*, 203:88-99, 1991.
Johnstone et al., In: *Immunochemistry in Practice*, Blackwell Scientific Publications, Oxford, 1982.
Judge et al., *Infect. Immun.*, 72:168-175, 2004.
Kaeppler et al., *Plant Cell Rep.*, 8:415-418, 1990.
Kaneda et al., *Science*, 243:375-378, 1989.
Kanevski et al., *Plant J.*, 2:457-463, 1992.
Kato et al, *J. Biol. Chem.*, 266:3361-3364, 1991.
Kraus et al. *FEBS Lett.*, 428(3):165-170, 1998.
Kwoh et al., *Proc. Natl. Acad. Sci. USA*, 86:1173, 1989.
Lareyre et al., *J. Biol. Chem.*, 274(12):8282-8290, 1999.
Latham and Galarza, *J. Virol.*, 75:6154-6165, 2001.
Laufs et al., *Biochimie*, 77:765-773, 1995a.
Laufs et al., *Proc. Natl. Acad. Sci. USA*, 92:3879-3883, 1995b.
Lazarowitz, *Crit. Rev. Plant Sci.*, 11:327, 1992.
Lee et al., *Biochem. Biophys. Res. Commun.*, 238(2):462-467, 1997.
Levenson et al., *Hum. Gene Ther.*, 9(8):1233-1236, 1998.
Ma et al., *Nat. Rev. Genet.*, 4:794-805, 2003.
Ma et al., *Trends Plant Sci.*, 10:580-585, 2005.
MacBeath and Schreiber, *Science*, 289(5485):1760-1763, 2000.
Macejak and Sarnow, *Nature*, 353:90-94, 1991.
Marillonnet et al., *Proc. Natl. Acad. Sci. USA*, 101:6852-6857, 2004.
Mason et al., *Proc. Natl. Acad. Sci. USA*, 93:5335-5340, 1996.
Matzke and Matzke, *Curr Opin. Plant Biol.*, 1:142-148, 1998.
McAleer et al., *Nature*, 307:178-180, 1984.
Mernaugh et al., In: *Molecular Methods in Plant Pathology*, Singh et al. (Eds.), CRC Press Inc., Boca Raton, Fla., 359-365, 1995.
Mor et al., *Biotechnol. Bioeng.*, 81:430-437, 2003.
Nakamura et al., In: *Handbook of Experimental Immunology* ($4^{th}$ Ed.), Weir et al., (eds). 1:27, Blackwell Scientific Publ., Oxford, 1987.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Nuttall et al., *Eur J. Biochem.*, 269:6042-6051, 2002.
Ohara et al., *Proc. Natl. Acad. Sci. USA*, 86:5673-5677, 1989.
Omirulleh et al., *Plant Mol. Biol.*, 21(3):415-428, 1993.
Palmer and Rybicki, *Adv. Virus Res.*, 50183-234, 1998.
Palmer et al., *Mol. Cell. Neurosci.*, 8:389-404, 1997.
Pandey and Mann, *Nature*, 405(6788):837-846, 2000.
PCT Appln. PCT/US87/00880
PCT Appln. PCT/US89/01025
PCT Appln. WO 88/10315
PCT Appln. WO 89/06700
PCT Appln. WO 94/09699
PCT Appln. WO 95/06128
Pelletier and Sonenberg, *Nature*, 334(6180):320-325, 1988.
Potrykus et al., *Mol. Gen. Genet.*, 199(2):169-177, 1985.
Pushko et al., *Vaccine*, 23:5751-5759, 2005.
Ridgeway, In: *Vectors: A Survey of Molecular Cloning Vectors and Their Uses*, Rodriguez et al. (Eds.), Stoneham: Butterworth, 467-492, 1988.
Rippe, et al., *Mol. Cell Biol.*, 10:689-695, 1990.
Sambrook and Russell, Molecular Cloning: A Laboratory Manual $3^{rd}$ Ed., Cold Spring Harbor Laboratory Press, 2001.
Sambrook et al., In: *Molecular cloning: a laboratory manual*, $2^{nd}$ Ed., Cold Spring Harbor Laboratory Press, Cold Spring Harbor, N.Y., 1989.
Santi et al., *Proc. Natl. Acad. Sci. USA*, 103:861-866, 2006.
Santi et al., *Vaccine*, 26:1846-1854, 2008.
Stoger et al., *Curr Opin. Biotechnol.*, 16:167-173, 2005.
Temin, In: *Gene Transfer*, Kucherlapati (Ed.), NY, Plenum Press, 149-188, 1986.
Tigges et al., *J. Immunol.*, 156(10):3901-3910, 1996.
Timmermans et al., *Annu. Rev. Plant Physiol.*, 45:79, 1994.
Tsuda et al., *Vox Sang*, 74:148-155, 1998.
Tsumaki et al., *J. Biol. Chem.*, 273(36):22861-22864, 1998.
Twyman et al., *Expert Opin. Emerg. Drugs*, 10:185-218, 2005.
Vitale and Pedrazzini, *Mol. Interv.*, 5:216-225, 2005.
Voinnet et al., *Cell.*, 95(2):177-187, 1998
Voinnet et al., *Plant J.*, 33:949-956, 2003.
Walker et al., *Proc. Natl. Acad. Sci. USA*, 89:392-396, 1992.
Wilson et al., *Science*, 287:1664-1666, 2000.
Wong et al., *Gene*, 10:87-94, 1980.
Wu et al., *Biochem. Biophys. Res. Commun.*, 233(1):221-226, 1997.
Yusibov et al., *Drugs RD*, 7:203-217, 2006.
Zhang and Mason, *Biotechnol. Bioeng.*, 93:271-279, 2006.
Zhao-Emonet et al., *Biochim. Biophys. Acta*, 1442(2-3):109-119, 1998.

The invention claimed is:

1. A method of producing a product of interest in a plant cell comprising:
    obtaining a first nucleic acid segment comprising at least one promoter, a short intergenic region (SIR) of a geminivirus genome, and a region encoding a first part of the product of interest, wherein the region encoding the first part of the product of interest is flanked on either side by at least a portion of a long intergenic region (LIR) of a geminivirus genome;
    obtaining a second nucleic acid segment comprising at least one promoter, a short intergenic region (SIR) of a geminivirus genome, and a region encoding a second part of a product of interest, wherein the region encoding the second part of the product of interest is flanked on either side by at least a portion of a long intergenic region (LIR) of a geminivirus genome;
    obtaining a third nucleic acid segment comprising a promoter and a nucleic acid encoding a Rep/RepA protein of a geminivirus genome;
    introducing the first nucleic acid segment, the second nucleic acid segment and the third nucleic acid segment into a plant cell to cause concomitant transient expression of the nucleic acid segments; and
    producing the product of interest in the plant cell by transient expression of the nucleic acid segment encoding the first and second parts of the product of interest;
    wherein the first nucleic acid segment and the second nucleic acid segment are separate replicons and are non-competing.

2. A vector system comprising:
    a first nucleic acid segment comprising at least one promoter, a short intergenic region (SIR) of a geminivirus genome, and a region encoding a first part of a product of interest, wherein the region encoding a the first part of the product of interest is flanked on either side by at least a portion of a long intergenic region (LIR) of a geminivirus genome;

a second nucleic acid segment comprising at least one promoter, a short intergenic region (SIR) of a geminivirus genome, and a region encoding a second part of a product of interest, wherein the region encoding the second part of the product of interest is flanked on either side by at least a portion of a long intergenic region (LIR) of a geminivirus genome; and a third nucleic acid segment comprising a promoter and a nucleic acid encoding a Rep/RepA protein of a geminivirus genome;

wherein the first nucleic acid segment and the second nucleic acid segment are separate replicons and are non-competing;

and wherein the first nucleic acid segment and the second nucleic acid segment and the third nucleic acid segment are comprised in a single vector.

3. The vector system of claim 2, further comprising a fourth nucleic acid segment that comprises a promoter and a gene-silencing inhibitor.

4. The vector system of claim 3, wherein the gene-silencing inhibitor is a P19 gene-silencing inhibitor from tomato bushy stunt virus.

5. The method of claim 1, wherein the first part and/or the second part of the product of interest is a nucleic acid, protein, polypeptide, or peptide.

6. The method of claim 1, wherein the first part and/or the second part of the product of interest is an antigen.

7. The method of claim 6, wherein the antigen is a hepatitis B core antigen (HBc) or a Norwalk Virus capsid protein (NVCP).

8. The method of claim 1, wherein the first nucleic acid segment, the second nucleic acid segment and the third nucleic acid segment are comprised in respective first, second and third vectors.

9. The method of claim 1, wherein the first nucleic acid segment, the second nucleic acid segment and the third nucleic acid segment are comprised in a single vector.

10. The method of claim 1, further comprising: obtaining a fourth nucleic acid segment comprising a promoter and a gene silencing inhibitor, and introducing the fourth nucleic acid segment into said plant cell.

11. The method of claim 10, wherein the gene-silencing inhibitor is a P19 gene-silencing inhibitor from tomato bushy stunt virus.

12. The method of claim 10, wherein the first nucleic acid segment, the second nucleic acid segment, the third nucleic acid segment and the fourth nucleic acid segment are comprised in respective first, second, third and fourth vectors.

13. The method of claim 10, wherein the first nucleic acid segment, the second nucleic acid segment, the third nucleic acid segment and the fourth nucleic acid segment are comprised in a single vector.

14. The method of claim 5, wherein the protein, polypeptide, or peptide raises an immune response when introduced into an animal.

15. The method of claim 14, wherein the product of interest is an antibody.

16. The method of claim 15, wherein the antibody is a monoclonal antibody.

17. The method of claim 16, wherein the monoclonal antibody is protective against Ebola virus GP1 (6D8).

18. The method of claim 17, wherein the first nucleic acid segment is that of vector pBY-H(6D8), as depicted in FIG. 1, and wherein the second nucleic acid segment is that of vector pBY-L(6D8), as depicted in FIG. 1.

19. The vector system of claim 2, wherein the first part and/or the second part of the product of interest is a nucleic acid, protein, polypeptide, or peptide.

20. The vector system of claim 2, wherein the first part and/or the second part of the product of interest is an antigen.

21. The vector system of claim 20, wherein the antigen is a hepatitis B core antigen (HBc) or a Norwalk Virus capsid protein (NVCP).

22. The vector system of claim 19, wherein the protein, polypeptide, or peptide raises an immune response when introduced into an animal.

23. The vector system of claim 22, wherein the product of interest is an antibody.

24. The vector system of claim 23, wherein the antibody is a monoclonal antibody.

25. The vector system of claim 24, wherein the monoclonal antibody is protective against Ebola virus GP1 (6D8).

26. The vector system of claim 25, wherein the vector is pBY-HL(6D8).R, whose T-DNA region is depicted in FIG. 1.

* * * * *